(12) United States Patent
Stevens et al.

(10) Patent No.: US 7,181,884 B2
(45) Date of Patent: *Feb. 27, 2007

(54) MATERIALS AND METHODS FOR CONTROLLING PESTS

(75) Inventors: Bruce R. Stevens, Gainesville, FL (US); James P. Cuda, Gainesville, FL (US); Lewis S. Long, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 589 days.

This patent is subject to a terminal disclaimer.

(21) Appl. No.: 10/298,974

(22) Filed: Nov. 18, 2002

(65) Prior Publication Data

US 2003/0140371 A1   Jul. 24, 2003

Related U.S. Application Data

(63) Continuation-in-part of application No. 09/991,458, filed on Nov. 16, 2001, now Pat. No. 6,766,613.

(51) Int. Cl.
*A01M 1/20* (2006.01)
*A01N 25/00* (2006.01)
*A01N 25/12* (2006.01)
*A01N 31/00* (2006.01)

(52) U.S. Cl. ............................ 43/132.1; 514/2; 514/12
(58) Field of Classification Search ..................... None
See application file for complete search history.

(56) References Cited

U.S. PATENT DOCUMENTS 6,766,613 B2 *   7/2004   Stevens et al. ............ 43/132.1

OTHER PUBLICATIONS

Barbehenn, R.V., et al., "Reassessment of the roles of the peritrophic envelope and hydrolysis in protecting polyphagous grasshoppers from ingested hydrolyzable tannins", *J. Chem Ecol.* (1996), 22:1911-1929.
Bayon, C., "Volatile fatty acids and methane production in relation to anaerobic carbohydrate frementation in *Oryctes nasicomis* larvae (Coleoptera: Scarabaeidae)", *J. Insect Physiol.* (1980), 26:819-828.
Bignell, D.E., and Anderson, J.M., "Determination of pH and oxygen status in the guts of lower and higher termites", *J. Insect Physiol.* (1980), 26:183-188.
Bounias, Michael, Christian P. Vivarés, Bonaventure Nizeyimana "Functional Relationships between Free Amino Acids in the Hemolymph of Fourth Instar larvae of the Mosquito *Aedes aegypti* (Diptera, Culicidae) as a Basis for Toxicological Studies" *Journal of Invertebrate Pathology*, 1989, pp. 16-22, vol. 54.
Broadway, R.M., and Villani, M.G., "Does host range influence susceptibility of herbivorous insects to non-host plant proteinase inhibitors?", *Entomol. Exp. et Appl.* (1995), 76:303-312.

Castagna, Michela, Chairat Shayakul, Davide Trotti et al. "Cloning and Characterization of a Potassium-coupled Amino Acid Transporter" *Proc. Natl. Acad. Sci. USA*, Apr. 1998, pp. 5395-5400, vol. 95.
Chaput, R. L. and J. N. Liles "Free and Peptide-Bound Amino Acids During the Larval and Pupal Stages of the Yellow-Fever Mosquito, *Aedes aegypti*" *Annals of the Entomological Society of America*, Jul. 1969, pp. 742-747, vol 62, No. 4.
Christensen, Halvor N. "Role of Amino Acid Transport and Countertransport in Nutrition and Metabolism" *Physiological Reviews*, Jan. 1990, pp. 43-77, vol. 10, No. 1.
Dadd, R. H., "Insect Nutrition: Current Developments and Metabolic Implications" *Ann Rev Entomol*, 1973, pp. 381-420, vol. 18.
Dadd, R.H., "Alkalinity within the midgut of mosquito larvae with alkaline-active digestive enzymes", *J. Insect Physiol.* (1975), 21:1847-1853.
Dow, J.A.T., and O'Donnell, M.J., "Reversible alkalinization by *Manduca sexta* midgut" *J. Exp. Biol.* (1990), 150:247-256.
Engelmann, F., and Geraerts, P.M., "The proteases and the protease inhibitor in the midgut of *Leucophaea maderae*", *J. Insect Physiol.* (1980), 26:703-710.
Evans, W.A.L. and Payne, D.W., "Carbohydrases of the alimentary tract of the desert locust, *Schistocerca gregaria* Forsk", *J. Insect Physiol.* (1964), 10:657-674.
Feldman, Daniel H., William R. Harvey, and Bruce R. Stevens "A Novel Electrogenic Amino Acid Transporter is Activated by $K^+$ or $Na^+$, Is Alkaline pH-dependent, and is $Cl^-$-independent" *The Journal of Biological Chemistry*, Aug. 11, 2000, pp. 24518-24526, vol. 275, No. 32.
Gerencser, George A. and Bruce R. Stevens "Thermodynamics of Symport and Antiport Catalyzed by Cloned or Native Transporters" *J. Exp. Biol.*, 1994, pp. 59-75, vol. 196.
Gräf, Frans J. S. Novak, William R. Harvey and Helmut Wieczorek "Cloning and sequecing of cDNA encoding the putative insect plasma membrane V-ATPse subunit A" *FEBS*, Mar. 1992, pp. 119-122, vol. 300, No. 2.
Harvey, William R., Simon H. P. Maddrell, William H. Telfer and Helmut Wieczorek "$H^+$ V-atpASES Energize Animal Plasma Membranes for Secretion and Abosrption of Ions and Fluids" *Amer. Zool.*, 1998, pp. 426-441, vol. 38.
Harvey, William R. and Helmut Wieczorek "Animal Plasma Membrane Energization by Chemiosmotic $H^+$ V-ATPases" *The Journal of Experimental Biology*, 1997, pp. 203-216, vol. 200.

(Continued)

*Primary Examiner*—Ashwin Mehta
(74) *Attorney, Agent, or Firm*—Saliwanchik, Lloyd & Saliwanchik

(57) ABSTRACT

The present invention provides materials and methods for pest control. The subject invention provides pesticidal compositions that contain one or more compounds that interact with organic solute transporter/ligand-gated ion channel multifunction polypeptides in the pest, and/or alter amino acid metabolic pathways, and/or alter ionic homeostasis in the pest. Upon exposure to a target pest, these compositions either compromise pest growth and/or cause the death of the pest. In a preferred embodiment, the compositions of the subject invention contain one or more amino acids and/or amino acid analogs. In a particularly preferred embodiment, the methods of the subject invention involve exposing a pest to a composition that comprises methionine or leucine, or an analog thereof.

11 Claims, 6 Drawing Sheets

OTHER PUBLICATIONS

Jaffe, J. J. and L. R. Chrin "De Novo Synthesis and Methionine in Normal and Brugia-Infected *Aedes Aegypti*" *J. Parasitol*, 1979, pp. 550-554, vol. 65, No. 4.

Kilberg, Michael S., Bruce R. Stevens and Donald A . Novak "Recent Advances in Mammalian Amino Acid Transport" *Annu. Rev. Nutr.*, 1993, pp. 137-165, vol. 13.

Korochkina, Svetlana E., Alexey V. Gordadze, Stanislav O. Zakharkin, Helen Benes "Differential Accumulation and Tissue Distribution of Mosquito Hexamerins During Metamorphosis" *Insect Biochem. Molec. Biol.*, 1997, pp. 813-824, vol. 27, No. 10.

Krishna, S.S., and Saxena, K.N., "Digestion and absorption of food in *Tribolium castaneum* (Herbst.)", *Physiol. Zool.* (1962), 35:66-78.

Kyte, Jack and Russell F. Doolittle "A Simple Method for Displaying the Hydropathic Character of a Protein" *J. Mol. Biol.*, 1982, pp. 105-132, vol. 157.

Mailliard, Mark E., Bruce R. Stevens, Giovanni E. Mann "Amino Acid Trnasport by Small Intestinal, Hepatic, and Pancreatic Epithelia" *Gastroenterology*, 1995, pp. 888-910, vol. 108.c.

Malandro, Marc S. and Michael S. Kilberg "Molecular Biology of Mammalian Amino Acid Transporters" *Annu. Rev. Biochem.*, 1996, pp. 305-336, vol. 65.

Martin, J.S., et al., "Failure of tannic acid to inhibit digestion or reduce digestibility of plant protein in gut fluids of insect herbivores: Implications for theories of plant defense", *J. Chem. Ecol.* (1987), 13:605-621.

Martin, M.M., et al. "The Disgestion of Protein and Carbohydrate by the Stream Detritivore, Tipula-Abdominalis (Diptera, Tipulidae)", *Oecologia* (1980), 46(3):360-364.

Martin, M.M., et al., "Digestive enzymes of larvae of three species of caddisflies (Trichoptera)", *Insect Biochem.* (1981a), 11:501-505.

Martin, M.M., et al., "The digestive enzymes of detritus-feeding stonefly nymphs (Plecoptera; Pteronarcyidae)", *Can. J. Zool.* (1981b), 59:1947-1951.

Mbungu, David, Linda S. Ross and Sarjeet S. Gill "Cloning, Functional Expression, and Pharmacology of a GABA Transporter from *Manduca Sexta*" *Archives of Biochemistry and Biophysics*, Apr. 20, 1995, pp. 489-497, vol. 318, No. 2.

Merzendorfer, Hans, Ralph Gräf, Markus Huss, William R. Harvey and Helmut Wieczorek "Regulation of Proton-Translocating V-ATPases" *The Journal of Experimental Biology*, 1997, pp. 225-235, vol. 200.

Mishra, S.C., and Sen-Sarma, P.K., "Hydrogen ion concentration in the digestive tract of three species of Indian termites", *Entomon.* (1981), 6:131-134.

Murdock, L.L., et al., "Cysteine digestive proteinases in Coleoptera", *Comp. Biochem. Physiol.* (1987), 87B:783-787.

O'Riordan, A.M. "Electrolyte movement in the isolated midgut of the cockroach (*Periplaneta americana*)", *J. Exp. Biol.* (1969), 51:699-714.

Patrick, Marjorie and Timothy J. Bradley "Regulation of Compatible Solute Accumulation in Larvae of the Mosquito *Culex Tarsalis*: Osmolarity Versus Salinity" *The Journal of Experimental Biology*, 2000, pp. 831-839, vol. 203.

Quick, Matthias and Bruce R. Stevens "Amino Acid Transporter CAATCH1 Is Also an Amino Acid-gated Cation Channel" *The Journal of Biological Chemistry*, Sep. 7, 2001, pp. 33413-33148, vol. 276, No. 36.

Stevens, Bruce R. "Amino Acid Transport in Intestine" *In: Mammalian Amino Acid Transport: Mechanisms and Control*, 1992, pp. 149-164, M.S. Kilberg and D. Haussinger, eds., Plenum, New York.

Stevens, Bruce R. "Membrane Transport of Nutrients" *In: Surgical Research*, 2001, pp. 845-856, W.W. Souba and D.W. Wilmore, eds., Academic Press, San Diego.

Stevens, Bruce R. "Digestion and Absorption of Protein" *In Biochemical and Physiological Aspects of Human Nutrition*, 1999, Chapter 6, pp. 107-123, M.H. Stipanuk, ed., W.B. Saunders Co., Philadelphia.

Teo, L.H., "Tryptic and chymotryptic activites in different parts of the gut of the field cricket *Gryllus bimaculatus* (Orthoptera: Gryllidae)", *Annals of the Entomological Society of America* (1997), 90(1):69-74.

Thomas, K.K., and Nation, J.L., "Protease, amylase and lipase activities in the midgut and hindgut of the cricket, *Gryllus rubens* and mole cricket, *Scapteriscus acletus.*" *Comp. Biochem. Physiol.* 79A:297-304.

Undeen, A.H. and Berl, D., "Laboratory Studies on the Effectiveness of Bacillus-Thuringiensis Var Israelensis-De-Barjac Against Simulium-Damnosum (Diptera, Simuliidae) Larvae", *Mosquito News* (1979), 39(4):742-745.

Waterhouse, D.F., and Stay, B., "Functional differentiation in the midgut epithelium of blowfly larvae as revealed by histochemcial tests", *Aust. J. Biol. Sci.* (1955), 8:253-277.

\* cited by examiner

MATERIALS AND METHODS FOR CONTROLLING PESTS

CROSS-REFERENCE TO RELATED APPLICATION

This application is a continuation-in-part of U.S. application Ser. No. 09/991,458 filed Nov. 16, 2001, now U.S. Pat. No. 6,766,613.

GOVERNMENT SUPPORT

The subject invention was made with funding from the National Institutes of Health (Grant No. AI 030464). Accordingly, the government may have certain rights in this invention.

BACKGROUND OF INVENTION

A longstanding worldwide demand exists for new, effective, environmentally friendly, and safe means to control pests that damage agriculture or serve as disease vectors. Agriculture costs incurred by pests exceed billions of dollars annually in decreased crop yields, reduced crop quality, increased harvesting costs, pesticide application costs, and negative ecological impact. In addition to agriculture pests, many blood-feeding insects and cockroaches are vectors for pathogenic microorganisms that threaten human and animal health, or are annoying at the least. As in the case of agriculture pests, direct and intangible costs incurred by blood-feeding and household pests concern pesticide safety hazards to humans and animals, bioaccumulation and environmental incompatibility, and synthesis and application costs.

Almost all field crops, nursery and horticulture plants, and commercial farming areas are susceptible to attack by one or more pests. Particularly problematic are Coleopteran and Lepidopteran pests. An example of a Lepidopteran pest is the hornworm larva of *Manduca sexta*, and an example of a Coleopteran pest is the Colorado potato beetle, *Leptinotarsa decemlineata*. Vegetable and cole crops, lentils, leafy vegetables, melons, peppers, potatoes and related tubers, tomatoes, cucumbers and related vine crops, as well as a variety of spices are sensitive to infestation by one or more pests including loopers, armyworms, moth larvae, budworms, webworms, earworms, leafeaters, borers, cloverworms, melonworms, leafrollers, various caterpillars, fruitworms, hornworms, and pinworms. Likewise, pasture and hay crops such as alfalfa, pasture and forage grasses and silage are often attacked by a variety of pests including armyworms, alfalfa caterpillars, European skipper, a variety of loopers and webworms, as well as yellowstriped armyworms.

Fruit (including citrus), nut, and vine crops are susceptible to attack by a variety of pests, including sphinx moth larvae, cutworms, skippers, fireworms, leafrollers, cankerworms, fruitworms, girdlers, webworms, leaffolders, skeletonizers, shuckworms, hornworms, loopers, orangeworms, tortrix, twig borers, casebearers, spanworms, budworms, budmoths, and a variety of caterpillars and armyworms.

Field crops are targets for infestation by insects including armyworm, asian and other corn borers, a variety of moth and caterpillar larvae, bollworms, loopers, rootworms, leaf perforators, cloverworms, headworms, cabbageworms, leafrollers, podworms, cutworms, budworms, hornworms, and the like. Pests also frequently feed upon bedding plants, flowers, ornamentals, vegetables, container stock, forests, fruit, ornamental, shrubs and other nursery stock. Even turf grasses are attacked by a variety of pests including armyworms and sod webworms.

For the past 50 years growers, health officials, and the public have depended on chemical pesticides for controlling a variety of pests. However, environmental experts, health officials, and the public have become concerned about the amount of residual chemicals found in food, ground water, and elsewhere in the environment. Regulatory agencies around the world are restricting and/or banning the uses of many synthetic pesticides, particularly those that are persistent in the environment and that enter the food chain. Stringent new restrictions on the use of pesticides and the elimination of some effective pesticides from the market place could limit economical and effective options for controlling costly pests. Some synthetic chemical pesticides poison the soil and underlying aquifers, pollute surface waters as a result of runoff, and destroy non-target life forms. These synthetic chemical pest control agents have the further disadvantage of presenting public safety hazards when they are applied in areas where pets, farm animals, or children may come into contact with them. They can also pose health hazards to the people applying them, especially if the proper application techniques are not followed.

Because crops of commercial interest are often the targets of pests, environmentally sensitive methods for controlling or eradicating pest infestations are desirable in many instances. This is particularly true for farmers, nurserymen, growers, and commercial and residential areas which seek to control pest populations using environmentally friendly compositions.

The most widely used environmentally friendly pesticidal formulations developed in recent years have been microbial pesticides derived from the bacterium *Bacillus thuringiensis* ("B.t."). *B. thuringiensis* is a Gram-positive bacterium that produces proteins which are toxic to certain orders and species of pests. Many different strains of B.t. have been shown to produce insecticidal proteins. Compositions including B.t. strains which produce insecticidal proteins have been commercially-available and used as environmentally-acceptable insecticides because they are toxic to specific target pests, but are harmless to plants and other non-target organisms. The specificity of these toxins is often strain-specific, with certain toxins being active against a relatively narrow spectrum of pests. Indeed, many B.t. toxins have been identified that are active only against particular insect orders (e.g., dipterans, hymenopterans, coleopterans, etc.). This limitation prevents the use of a single B.t. endotoxin composition as a broad-range pesticide.

Crop pests are not the only targets for which an environmentally friendly and safe pesticide would be highly desirable. Many blood-feeding pests are known to prey on humans and animals, and many pests are vectors for pathogenic microorganisms that threaten human and animal health, including commercially important livestock, pets and other animals. The order Diptera contains a large number of blood-ingesting and disease-carrying pests, including, for example, mosquitoes, black flies, no-see-ums (punkies), horse flies, deer flies and tsetse flies.

Various species of mosquitoes, for example, transmit diseases caused by viruses, and many are vectors for disease-causing nematodes and protozoa. Mosquitoes of the genus *Anopheles* transmit Plasmodium, the protozoan that causes malaria. The mosquito species *Aedes aegypti* transmits an arbovirus that causes yellow fever in humans. Other viruses transmitted by *Aedes* species include the causative agents of dengue fever, eastern and western encephalitis, Venezuelan equine encephalitis, St. Louis encephalitis, chikungunya, oroponehe and bunyarnidera. The genus *Culex*, which includes the common house mosquito *C. pipiens*, is implicated in the transmission of various forms of encephalitis, filarial worms, and West Nile virus. *Trypanasoma cruzi*, the causative agent of Chagas disease, is transmitted by various species of blood ingesting Triatominae bugs. Tsetse flies (*Glossina* spp.) transmit African trypanosomal diseases of humans and cattle. Other diseases are transmitted by various blood-ingesting pest species.

Various pesticides have been employed in efforts to control or eradicate populations of disease-transmitting pests. For example, DDT, a chlorinated hydrocarbon, has been used in attempts to eradicate malaria-bearing mosquitoes throughout the world. Other examples of chlorinated hydrocarbons are BHC, lindane, chlorobenzilate, methoxychlor, and the cyclodienes (e.g., aldrin, dieldrin, chlordane, heptachlor, and endrin). The long-term stability of many of these pesticides and their tendency to bioaccumulate render them particularly dangerous to many non-target organisms.

In addition to environmental concerns, another major problem associated with conventional chemical control practices is the capability of many species to develop pesticide resistance. Resistance results from the selection of naturally occurring mutants possessing biochemical, physiological or behavioral factors that enable the pests to tolerate the pesticide when it is applied.

There is clearly a longstanding need in the art for pesticidal compounds that reduce or eliminate direct and/or indirect threats to human health posed by presently available pesticides, that are environmentally compatible and safe, are not toxic to non-pest organisms, and have a reduced tendency to bioaccumulate.

Approaches to pesticide development are lacking that involve specifically disrupting key pest regulatory processes, notably membrane organic solute transporters, organic solute- and amino acid-gated ion channel proteins, and/or amino acid metabolic pathways as targets. The development of such methodologies could provide safer, environmentally friendly alternatives to conventional commercially used pesticides, and provide more economical means for suppressing or eradicating target pest populations. The formulation of pesticidal compositions that are non-toxic to animals and to humans would greatly enhance the present methods available for killing pests, and would provide alternative strategies for environmentally responsible pest management.

Membrane organic solute transporter proteins and ion channel proteins serve critical roles in maintaining organic solute and ionic metabolic, thermodynamic, and electrical events in cells. In both eukaryotes and prokaryotes these proteins affect electrochemical gradients of a wide variety of metabolic molecules and electrolytes, including amino acids and related metabolites as well as $H^+$, $OH^-$, $Na^+$, $K^+$, $Cl^-$, and carbonate ions (Gerencser and Stevens, 1994 *J. Exper. Biol.* 196:59–75; Stevens, B. R. 2001. "Theory and methods in nutrient membrane transport." In: *Surgical Research*. pp. 845–856. W. W. Souba and D. W. Wilmore, eds., Academic Press, San Diego). Molecular cloning studies have identified several subfamilies of organic solute transporters and ion channels (Griffith, J. K. and C. E. Sansom, 1998, In: The Transporter Facts Book, Academic Press, San Diego, pp. 500).

Organic solute transporters and ion channels are commonly defined by their substrate selectivity within polypeptide superfamilies. For cloned or native secondary active transporters, it is generally assumed that cell membranes utilize ion and organic molecule electrochemical gradients to aid in exchanging these solutes between the cell interior and extracellular environment (Gerencser, G. A. and B. R. Stevens, 1994, *J. Exper. Biol.* 196:59–75; Stevens, B. R. 1999, Digestion and Absorption of Protein. In: Biochemical and Physiological Aspects of Human Nutrition. pp. 107–123, M. H. Stipanuk, ed., W.B. Saunders Co., Philadelphia). In the 'prototypical' transporter, organic solutes that can be moved across cell membranes by uniport, heteroor homo-exchange, and/or uptake can be activated by ions, and/or thermodynamiclly cotransported with ions (cf refs in Quick, M. and B. R. Stevens, 2001, *J. Biol. Chem.* 276(36): 33413–33418; Griffith, J. K. and C. E. Sansom, 1998, In: The Transporter Facts Book, Academic Press, San Diego, pp. 500). Ion channels, on the other hand, are typically distinct from organic solute transporters, are selective in their conducting ion species, and may be gated by organic ligands (Hille, B, 2001, *Ionic channels of excitable membranes*, $3^{rd}$ Edition, Sinauer Associates, Inc., Sunderland, Mass., pp. 814; Saier, M. H., 2000, Families of proteins forming transmembrane channels. *J. Membrane Biol.* 175: 165–180). In some cases, multimeric (e.g., heterodimer, homodimer) interactions or associations among or between several polypeptides are responsible for the physiological activity of solute transport or ion conductance, or multifunctional solute transport/ion channel activity (Saier, M. H., 2000, A functional-phylogenetic classification system for transmembrane solute transporters, *Micro. Molec. Biol. Rev* 64:354–411; Verrey, F., Jack, D. L., Paulsen, I. T., Saier, M. H., and Pfeiffer, R., 1999, New glycoprotein-associated amino acid transporters, *J. Membrane Biol.*, 172:181–192; Saier, M. H., 2000, Families of transmembrane transporters selective for amino acids and their derivatives, *Microbiology*, 146:1775–1795; Wagner, C. A., Lang, F., and Broer, S., 2001, Function and structure of heterodimeric amino acid transporters, *Am. J. Physiol. Cell Physiol.*, 281: C1077–C1093; Kanai, Y., and Endou, H., 2001, Heterodimeric amino acid transporters: molecular biology and pathological and pharmcological relevance, *Curr. Drug Metabol.*, 2:339–354; Saier, M. H., 2000, Families of proteins forming transmembrane channels. *J. Membrane Biol.* 175:165–180). The amino acid/polyamine/choline (APC) superfamily of transporters represents examples of polypeptides responsible for amino acid transport. Within the APC superfamily, a subunit family of polypeptide light chains (e.g., LAT polypeptides) require association with an ancillary heavy chain polypeptide subunit of the 4F2hc/CD98 family, for functional membrane transport activity (Saier, M. H., 2000, A functional-phylogenetic classification system for transmembrane solute transporters, *Micro. Molec. Biol. Rev* 64:354–411; Verrey, F., Jack, D. L., Paulsen, I. T., Saier, M. H., and Pfeiffer, R., 1999, New glycoprotein-associated amino acid transporters, *J. Membrane Biol.*, 172:181–192; Wagner, C. A., Lang, F., and Broer, S., 2001, Function and structure of heterodimeric amino acid transporters, *Am. J. Physiol. Cell Physiol,.* 281:C1077–C1093; Kanai, Y., and Endou, H., 2001, Heterodimeric amino acid transporters: molecular biology and pathological and pharmcological relevance, *Curr. Drug Metabol.*, 2:339–354).

*Manduca sexta* is a major crop pest whose larval stage, commonly known as tobacco hornworms, rapidly attacks and defoliates tobacco and tomato plants; the large fifth instar larvae are especially damaging. Other vegetable crops such as peppers, eggplant, and potatoes also can be affected. Tobacco and tomato hornworms rapidly grow and gain weight as they progress from the first instar stage (about 6.7 mm) through the fifth instar (about 81.3 mm) over a period of about 20 days. The sated larvae then drop to the soil to pupate, and eventually emerge as adult moths. The moths lay eggs, which develop into larvae, and the life cycle continues, thereby sustaining crop damage. Killing the larvae prevents immediate crop damage and prevents or reduces future damage by interrupting the life cycle.

The midgut region of *Manduca sexta* larvae displays compartments with the property of high concentrations of primarily $K^+$ in an alkaline fluid (~pH 10), with transepithelial potentials ~250 mV (Harvey et al., 1999, *Am. Zol.* 38:426–441; Harvey and Wieczorek, 1997, *J. Exper. Biol.* 200:203–216). Epithelial cells of this region transport a variety of organic and inorganic solutes and nutrients, including amino acids and electrolytes, as demonstrated by in vitro isolated membrane vesicle uptake studies. In place of a $Na^+/K^+$-ATPase typically found in cells, this tissue instead possesses a proton translocating V-ATPase (Graf et al., 1992, *FEBS Lett.* 300:119–122; Merzendorfer et al. 1997, *J. Exper. Biol.* 200:225–235) which energizes the cell membranes for secretion and absorption of ions, primarily $K^+$ and $Na^+$, and establishment of a large pH gradient. A $K^+$-activated leucine-preferring transporter (KAAT1) has been identified from the hornworm midgut (Castagna et al., 1998, *Proc Natl. Acad. Sci. USA* 95:5395–5400), and a GABA (gamma aminobutyric acid) transporter has been cloned from an *Manduca sexta* embryo cDNA library (Mbungu et al. 1995, *Arch. Biochem. Biphys.* 318:489–497).

CAATCH1 (Cation-Amino Acid Transporter/CHannel) is a recently cloned insect membrane protein initially cloned from *Manduca Sexta*. CAATCH1 exhibits a unique polypeptide and nucleotide sequence related to, but different from, mammalian $Na^+$-, $Cl^-$-coupled neurotransmitter transporters (Feldman et al., 2000, *J. Biol. Chem.* 275:24518–24526). Utilizing a unique PCR-based strategy, the gene encoding CAATCH1 was cloned (Feldman et al., 2000, supra) from a cDNA library in LambdaZap plasmids, obtained from the digestive midgut of *Manduca sexta* larvae.

The unanticipated and novel biochemical, physiological, and molecular properties of CAATCH1 indicated that it is a multi-function protein that mediates amino acid uptake in a manner that is thermodynamically uncoupled from ion electrochemical potentials, and furthermore that CAATCH1 simultaneously functions as an amino acid-modulated gated alkali cation channel (Quick, M. and B. R. Stevens, 2001, "Amino acid transporter CAATCH1 is also an amino acid-gated cation channel". *J. Biol. Chem* 276:33413–33418) serving at least $Na^+$ and $K^+$. Radiotracer and electrophysiology experiments with functional CAATCH1 polypeptide expressed from the full length CAATCH1 cDNA demonstrated direct amino acid ligand-protein interactions, and indicated that binding by different amino acid substrates differentially affects the conformational states of CAATCH1 (Quick, M. and B. R. Stevens, 2001, *J. Biol. Chem.* 276: 33413–33418). Notably, L-methionine binding to CAATCH1 in situ in biomembranes in the presence of $Na^+$ perturbs the charge-voltage relation with a high affinity binding constant, affecting transient currents due to CAATCH1-associated charge transfer across the membrane dielectric field. Furthermore, CAATCH1-associated voltage-dependent amino acid-elicited steady state inward cation currents are blocked by methionine, and indeed methionine reversed charge movements via CAATCH1 expressed in cell membranes, even though radiotracer methionine influx is catalyzed by CAATCH1 (Quick, M. and B. R. Stevens, 2001, *J. Biol. Chem.* 276:33413–33418). In insects, CAATCH1 likely plays a broader role than that of a 'classical' transporter or channel; as a multifunction protein CAATCH1 is likely a key protein in electrolyte and organic solute homeostasis of certain insects (Feldman et al, 2000, *J. Biol. Chem.* 275(32):24518–24526)

Many pests—including mosquitoes, black flies, cockroaches, Lepidopterans, and Coleopterans—possess an alkaline pH midgut, and share some similar physiological mechanisms that occur within this unusual milieu (Nation, J., 2001, In: Insect Physiology and Biochemistry, CRC Press, Boca Raton, pp 496). Mosquito larvae possess such an alkaline midgut, and adjust free amino acid concentrations in their hemolymph and extracellular compartments in direct response to existence of foreign factors in the gut (e.g., B.t. δ-endotoxin) or the salinity of their habitat (Bounias, M. et al., 1989, *J. Invertebr Pathol.* 54:16–22). Notably, one standout free amino acid, L-proline, accumulates 4-fold during the normal course of *Aedes aegypti* larval development, and in *Culex* spp. L-proline accumulation can exceed 50-fold (up to 70 mM) when larvae are stimulated by $Na^+$ in their feeding pools (Bounias, M. et al., 1989, supra; Patrick, M. L. and T. J. Bradley, 2000, *J. Exp. Biol.* 203:831–839; Chaput, R. L. and J. N. Liles, 1969, *Ann. Entomol. Soc. Am.* 62:742–747). This proline is likely utilized as an energy source and for osmoregulation (Patrick, M. L. and T. J. Bradley, 2000, *J. Exp. Biol.* 203:831–839; Bounias et al., 1989, J. Invertebr Pathol. 54:16–22). In contrast, free L-methionine has the distinction of virtually the lowest measurable concentration ($\leq 0.001$ mM) of any of the free amino acids in mosquito larvae. Virtually all methionine existing in the free amino acid state in larvae (Dadd, R. H., 1973, *Ann Rev Entomol* 18:381–420) is metabolically shunted and sequestered into so-called methionine-rich hexamerin proteins (Korochkina et al., 1997, *Insect Biochem Mol. Biol.* 27:813–824) that are stored for post-larval developmental events. Methionine analogues have been shown to modify metabolism in Lepidopterans and other insects (Rock, G. C. et al., 1973, Utilization of methionine analogues by *Argyrotaenia velutinana* Larvae. *Ann Entomol Soc Am.* 66:177–179). In its role as a nutrient transporter, the CAATCH1 protein has been shown to be primarily responsible for proline uptake (Feldman et al., 2000, *J. Biol. Chem.* 275(32):24518–24526), while in the presence of extremely low concentrations of methionine, CAATCH1 effectively shuts down ionic fluxes via its channel properties (Feldman et al., 2000, J. Biol. Chem. 275(32):24518–24526; Quick, M. and B. R. Stevens, 2001, *J. Biol. Chem.* 276(36): 33413–33418).

Compared to conventional organic pesticides, the use of biodegradable small molecules, such as amino acids, as pesticides is highly desirable, owing to the safety of such compounds to humans, animals, and the environment.

BRIEF SUMMARY

The present invention provides materials and methods for pest control. In a preferred embodiment, the subject invention overcomes drawbacks inherent in the prior art by providing pesticidal compositions that contain one or more compounds that interact with organic solute transporter/ligand-gated ion channel multifunction polypeptides in the pest. Upon exposure, ingestion, or other means of absorption by a target pest, these compositions either compromise pest growth and/or cause the death of the pest. In a preferred embodiment, the compositions of the subject invention contain one or more amino acids and/or amino acid analogs.

In a preferred embodiment, the materials and methods of the subject invention achieve pest control by disrupting the function of a newly discovered class of multifunction solute transporter/ligand-gated ion channel proteins (the CAATCH proteins). The CAATCH protein in *Manduca sexta* (tobacco hornworm), designated as CAATCH1, exemplifies this class of proteins. In accordance with the subject invention, the CAATCH proteins have been found to be important in regulating electrolyte and organic solute fluxes, especially in a pest having an alkaline pH gut region. CAATCH1 is a multi-function polypeptide that mediates amino acid uptake in a manner that is thermodynamically uncoupled to ion electrochemical potentials, and furthermore CAATCH1 simultaneously functions as an amino acid-modulated gated alkali cation channel serving at least $Na^+$ and $K^+$.

In accordance with the subject invention, effective pest control is achieved by disrupting the function of a CAATCH polypeptide and/or related molecules or groups of molecules, including solute transporter/ion channel polypeptides as monomers or manifesting activity (solute transport, ion channel, or both functions) as a multimeric arrangement of different polypeptides (e.g., multimers, heterodimers, etc), or same polypeptides (e.g. homodimers, homotetramers, etc). Also in accordance with the subject invention, effective pest control is achieved by altering pest cell intracellular/membrane trafficking mechanisms or pathways that direct CAATCH, or CAATCH-like proteins or their regulatory subunits, to the plasma membrane.

For convenience, reference is made herein to achieving pest control by disrupting CAATCH proteins, or, specifically, CAATCH1. It should be understood that such reference is not just to disrupting the CAATCH1 protein of *Manducta Sexta* but also to other CAATCH proteins and, more generally, to proteins which are involved individually or in combination with the CAATCH functions, as described herein.

As described herein, the function of the CAATCH proteins, and related proteins, can be disrupted in a number of ways to achieve the desired pest control. For example, in accordance with the subject invention, it has been found that small molecules, which interfere with these proteins, can be administered to a pest, or its situs, to achieve pest control. Specifically exemplified herein is the use of the amino acids methionine or leucine (and/or analogs thereof) to control pests. These compounds can be administered in a wide range of ways including the application of compositions comprising these individual amino acids (and/or their analogs, or bound to other molecules, for example by amide bonds), application of polypeptides which are made up of an abundance of these pesticidal amino acids, and providing a transgenic plant which expresses a pesticidal amount of the amino acids as either free amino acids, as salts of amino acids or their analogs, or bound to other molecules, or existing in polypeptides.

In a preferred embodiment, the methods of the subject invention involve delivering to or applying to a pest a composition that comprises L-methionine or L-leucine, or an analog thereof. Exemplary analogs include, but are not limited to, methionine esters, leucine esters, D-methionine, D-leucine, D-tert-leucine, L-tert-leucine, DL-methionine, DL-leucine, L-methioninol, L-leucininol, L- or D-methioninemethylsulfonium chloride, L-methionine sulfone, L-methionine-DL-sulfoximine, seleno-DL-methionine, L-ethionine, L-methionine sulfoxide, L-methionine-D-hydroxy analog, small methionyl peptides, low molecular weight leucyl peptides, alphaketoisocaproic acid, and the like. Likewise, methyl or ethyl esters of such compounds are also contemplated to be useful, as are keto derivatives of such compounds.

In a specific embodiment, insect pests are controlled by administering methionine to the insects. Alternatively, other amino acids such as histidine, glycine, threonine, or alanine can also be used. For all embodiments involving compounds with chiral centers, the L-, D-, DL-, or partially racemic forms are also contemplated to be useful. Alternatively, amino acid analogs that do not possess chiral centers are contemplated to be useful.

Examples of target crops to be protected within the scope of the present invention comprise the crops referred to in the Background of the Invention and include the following plants: potato, tomato, eggplant, corn (maize), soybeans, tobacco, nuts, forage grasses, cereals, pomes and soft fruits, leguminous plants, oil plants, cucumber plants, fiber plants, citrus fruit, vegetables, lauraceae, deciduous trees and conifers, as well as ornamentals.

Although it is believed that the administration of amino acids to achieve pest control according to the subject invention is effective as a result of the disruption of particular proteins as described herein, one aspect of the subject invention is simply the control of pests by administering amino acids or their analogs, regardless of the specific mechanism involved.

One aspect of this invention contemplates altering methionine levels in pests by manipulating biochemical pathways leading to methionine production in target pests. Such manipulations include, but are not limited to, precursors and cofactors of methionine metabolic biosynthesis pathways.

The subject invention provides various other alternative approaches to disrupting the function of the unique newly discovered class of multifunction transporter/channel proteins or solute transporter/ion channel polypeptides. These other approaches include, for example, the use of interfering RNA (RNAi), gene silencing techniques, and antisense polynucleotides. In a specific embodiment, the antisense molecules are complementary to contiguous nucleotide sequences of at least about 15 nucleotides from SEQ ID NO:1. These antisense constructs can be used to "downregulate" the expression of CAATCH, and/or related proteins, and/or polypeptides associated with solute transport/ion channel activity, in a particular cell. Alternatively, antisense constructs complementary to a contiguous nucleotide sequence from the CAATCH1 promoter sequence may also be used to regulate the activity of CAATCH and/or related proteins. Alternatively, antisense constructs complementary to a contiguous sequence from functionally similar solute transporter/ion channel polypeptides. Antisense constructs are well-known in the art and include the use of antisense mRNA to reduce the transcription or translation or otherwise impair the net production of the encoded polypeptide.

The subject invention also provides methods for identifying compounds which regulate, alter, or modulate the biochemical and/or physiological functional activity of a CAATCH polypeptide or polynucleotide (or related molecules or regulatory subunits of solute transporter/ion channel systems, or which alters intracellular/membrane trafficking of CAATCH polypeptides or subunits of transporter/ion channel functional multimers). In one embodiment this method comprises exposing a cell that expresses a CAATCH polypeptide to at least one compound or signal whose ability to modulate the activity of the CAATCH polypeptide is sought to be determined, and thereafter monitoring the cell for a change that is a result of the modulation of activity of CAATCH or related polypeptide(s). Such an assay is particularly contemplated to be useful in the identification of cellular trafficking molecules, agonists, antagonists and/or allosteric modulators of CAATCH.

A further aspect of the invention provides methods for screening compounds (e.g., synthetic peptides, peptide analogs, peptidomimetics, small molecule inhibitors, etc.) which inhibit or reduce the binding of a CAATCH polypeptide or other solute transporter/ion channel polypeptide. According to this embodiment, screening for chemical or biochemical entities may be performed e.g., by means of a cell-based assay, an in vitro assay for CAATCH function and/or rational pesticidal formulation or amino acid transporter-active analogs, drugs, or compounds. Cell-based assays for screening can be designed e.g., by constructing cell lines in which the expression of a reporter protein, i.e. an easily assayable protein, is dependent on CAATCH activity. Such an assay enables the detection of compounds that directly antagonize CAATCH, or compounds that inhibit other cellular functions required for the activity of CAATCH. Compounds may also be identified which recognize or inhibit amino acid or other solute transport via the CAATCH1 polypeptide or modify ion flux through the CAATCH polypeptide. Example ions include, but are not limited to, $N^+$, $K^+$, $H^+$, $OH^-$, $Cl^-$, bicarbonate, and carbonate.

In another aspect, the present invention provides an antibody that is immunoreactive with a transporter/channel polypeptide or regulatory subunit polypeptides or cellular trafficking polypeptides of the invention. Reference to antibodies includes whole polyclonal and monoclonal antibodies, and parts thereof, either alone or conjugated with other moieties. The monoclonal antibodies of the present invention can be used in standard immunochemical procedures, such as immunoprecipitation, ELISA and Western blot methods. Also, immunoabsorbent protocols may be used in purifying native or recombinant peptide species or synthetic or natural variants thereof.

Advantageously, the amino acid-based targeted pesticides of the subject invention are environmentally safe due to target selectivity, low toxicity to humans and pets, and their biodegradation by environmentally friendly naturally occurring microorganisms. Also, the use of these pesticides is compatible with the use of natural enemies of pests (e.g., parasitoids and predators). In fact, L-methionine is an "essential or indispensable" amino acid in humans, meaning that L-methionine is not synthesized by the body but instead is a required nutrient in the diet needed to sustain human life (Fuller, M. F., 2000. "Protein and amino acid requirements", pp. 287–304 In: *Biochemical and Physiological Aspects of Human Nutrition*, M. H. Stipanuk, ed. W.B. Saunders Co., Philadelphia). Since it is a naturally occurring substance, the use of this compound and related amino acids contribute to a sustainable, pesticide-free food supply, and preserve the environment by reducing the reliance on traditional pesticides.

BRIEF DESCRIPTION OF SEQUENCES

Figure 1:
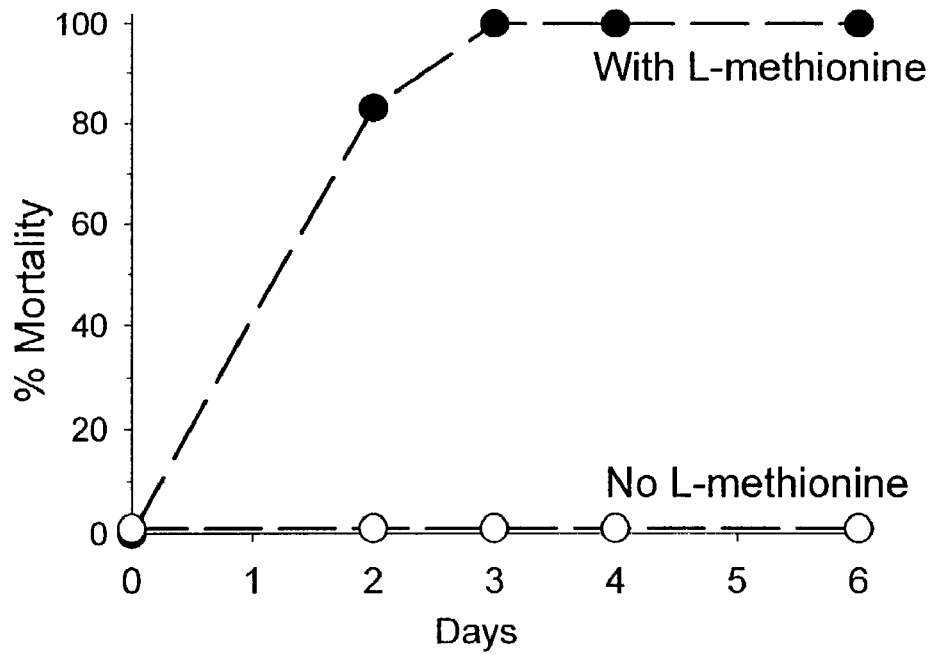
FIG. 1 shows the efficacy of L-methionine as a *Manduca sexta* pesticide using a defined laboratory diet administered ad libitum.

SEQ ID NO: 1 is a DNA sequence, including 5' and 3' untranslated regions and the open reading frame, that encodes the CAATCH1 protein of *Manduca sexta*.

SEQ ID NO: 2 is the predicted amino acid sequence of the CAATCH1 protein of *Manduca sexta*, based on the open reading frame of SEQ ID NO:1.

SEQ ID NOS: 3–27 are primers used as described herein to clone CAATCH genes.

DETAILED DISCLOSURE

The subject invention provides novel pest control compositions and methods for using such compositions. In one embodiment, the subject compositions can be used to control pests of agricultural crops. These pests include, for example, coleopterans (beetles), lepidopterans (caterpillars), and mites. The compounds of the subject invention can also be used to control household pests including, but not limited to, ants, termites, and cockroaches. The compounds can also be used to control mosquitoes such as *Aedes aegypti*, *Anopheles gambiae*, and *Culex* spp. Other biting pests such as flies, fleas, ticks, and lice can also be controlled using the compounds and methods of the subject invention. In a preferred embodiment, the materials and methods of the subject invention are used to control pests that have an alkaline gut compartment. Advantageously, the methods and materials of the subject invention provide a novel environmentally friendly and highly effective approach to controlling pests.

In a preferred embodiment, the methods of the subject invention involve providing access to, or applying to a pest, a composition that comprises methionine or leucine, or an analog thereof. Exemplary analogs include, but are not limited to, methionine esters, leucine esters, D-methionine, D-leucine, D-tert-leucine, L-tert-leucine, DL-methionine, DL-leucine, L-methioninol, L-leucininol, L- or D-methioninemethylsulfonium chloride, L-methionine sulfone, L-methionine-DL-sulfoximine, seleno-DL-methionine, L-ethionine, L-methionine sulfoxide, L-methionine-D-hydroxy analogue, small methionyl peptides, low molecular weight leucyl peptides, alphaketoisocaproic acid, and the like. Likewise, methyl or ethyl esters of such compounds are also contemplated to be useful, as are keto analogs of such compounds.

In a specific embodiment, pests are controlled by administering methionine to the pests. Alternatively, other amino acids such as histidine, glycine, threonine, alanine (including beta-alanine) or gamma aminobutyric acid (GABA) can also be used. Furthermore, organic solute substrates or ligands that bind to any pest solute transporter or solute-gated ion channel protein or multifunctional transporter-channel protein or protein complex can also be used. For all embodiments involving compounds with chiral centers, the L-, D-, DL-, or partially racemic forms are also contemplated to be useful. Alternatively, amino acid analogs that do not possess chiral centers are contemplated to be useful.

Methionine levels can be manipulated in the pest via at least two methionine synthetases (Jaffe, J. J. and L. R. Chrin, 1979, *J. Parisitol.* 65:550–554), E.C.2.1.1.13 and E.C.2.1.1.5. A further aspect of this invention concerns approaches to manipulate methionine levels in pests via metabolic pathways. In one embodiment, pests are controlled by altering the precursors and cofactors of methionine enzymatic biosynthesis, which includes but is not limited to manipulating levels of betaine, homocysteine, S-adenosylmethionine, 5-methyltetrahydofolate, and colbalamine and its derivatives including vitamin B12.

The materials and methods of the subject invention exert their pesticidal activity by disrupting a new category of ion-associated organic solute transporter/ion channel proteins (CAATCH) as monomers, or as part of a multimer (e.g., homodimer, heterodimer, etc.) The CAATCH1 protein of *Manduca sexta* typifies this new CAATCH class of proteins. This insect protein displays a dual role as an amino acid transporter and an amino acid ligand-gated ion channel. In its role as a nutrient transporter, the CAATCH protein has been shown to be primarily responsible for proline uptake, while in the presence of extremely low concentrations of methionine, CAATCH effectively shuts down ionic fluxes via its channel aspect (Feldman et al., 2000, *J. Biol. Chem.* 275:24518–24526; Quick, M. and B. R. Stevens, 2001, *J. Biol. Chem.* 276:33413–33418). The *Manduca sexta* CAATCH1 protein represents the first of its kind for a new class of membrane proteins. In a unique manner, the substrate selectivity of CAATCH is modulated by physiological conditions depending on the presence of either $K^+$ or $Na^+$ ion at alkaline pH. L-methionine modulates the CAATCH reaction mechanism by binding to CAATCH and blocking cation current via the ion channel aspect of the CAATCH polypeptide, and/or by interfering with or blocking the transport of amino acids. By interfering with the combined amino acid transporting/ligand-gated $K^+/Na^+$ ion channel properties of CAATCH, the homeostasis-maintaining role of the protein is perturbed and leads to disruption of fluid, electrolyte and nutrient movements within the organism.

Although the disruption of the function of the CAATCH1 protein from *Manduca sexta* is specifically exemplified herein, the materials and methods of the subject invention encompass the disruption of other related transporters, channels, or multifunction transporter/channel proteins, as monomers or in multimeric arrangements with itself or other polypeptides (e.g., including regulatory polpeptides), or disrupting intracellular/membrane trafficking pathways of related transporter/channel proteins and/or their regulatory subunits, in other target pests. Further, the subject invention contemplates direct inhibition of the CAATCH class of proteins as well as the disruption of the cascade of cellular physiological and biochemical activities associated with these types of transporter/channel proteins.

Pest control can be achieved according to the subject invention by inhibiting a member of, for example, the amino acid/polyamine/choline (APC) superfamily of transporters, a member of the light chain (LAT) family of transport polypeptides, or a member of the heavy chain group (e.g., 4f2hc/CD98) of ancillary polypeptides. Thus, the subject invention provides pesticidal compositions that contain one or more compounds that interact with organic solute transporter/ligand-gated ion channel multifunction polypeptides in the pest, and/or alter amino acid metabolic pathways, and/or alter ionic homeostasis in the pest. Upon exposure to a target pest, these compositions either compromise pest growth and/or cause the death of the pest.

For convenience, reference is made herein to achieving pest control by disrupting CAATCH. It should be understood that this is not just to disrupting the CAATCH1 protein of *Manducta Sexta* but also to other CAATCH proteins and, more generally, to proteins which are involved individually or in combination with the CAATCH functions.

As would be appreciated by one skilled in the art having the benefit of the instant disclosure, pest control can be achieved in a number of ways according to the subject invention. For example, compositions comprising individual pesticidal amino acids can be administered directly to the pests. Alternatively, these amino acids may be provided as components of polypeptides, other covalently linked polymers of amino acids or their analogs, or salts of amino acids or their analogs, which are then degraded to the individual amino acids or their analogs in the pest gut and/or prior to entry into the pest gut. These polypeptides or covalently linked compounds may be produced synthetically or recombinantly. In the case of recombinant production, the polypeptides may be produced, for example, in a microbial host followed by isolation of the polypeptide for subsequent administration. The microbial produced polypeptide may also be administered directly to the pest and/or its situs.

The methionine analogs and other amino acid analogs and/or polypeptides which contain the pesticidal amino acids of the subject invention may also be expressed or overexpressed in plant cells. The polypeptide may be isolated from the plant cell or, preferably, pest control is achieved by a pest ingesting the plant material. Furthermore pest control can be achieved by avoidance behavior whereby the deleterious effect to the host is reduced by, for example, the pest avoiding consumption of the plant.

One method for controlling pests according to the subject invention provides materials and methods for controlling pests by using double-stranded interfering RNA (RNAi), or RNA-mediated interference (RNAi). The use of antisense compounds is also contemplated.

In view of the use of recombinant hosts according to the subject invention, a further aspect of the subject invention is the polynucleotides that encode the pesticidal polypeptides. These polynucleotide sequences can be readily synthesized by a person skilled in the art, and can be used to transform an appropriate prokaryotic or eukaryotic host to enable the host to express the pesticidal compounds. Hosts of particular interest include bacteria, yeasts, viruses, and plants. For each of these hosts, the DNA sequences may be specifically designed by a person skilled in the art to utilize codons and regulatory sequences known to be optimally expressed in the particular hosts. Advantageous promoters can also easily be employed in the polynucleotide sequences.

Figure 9:
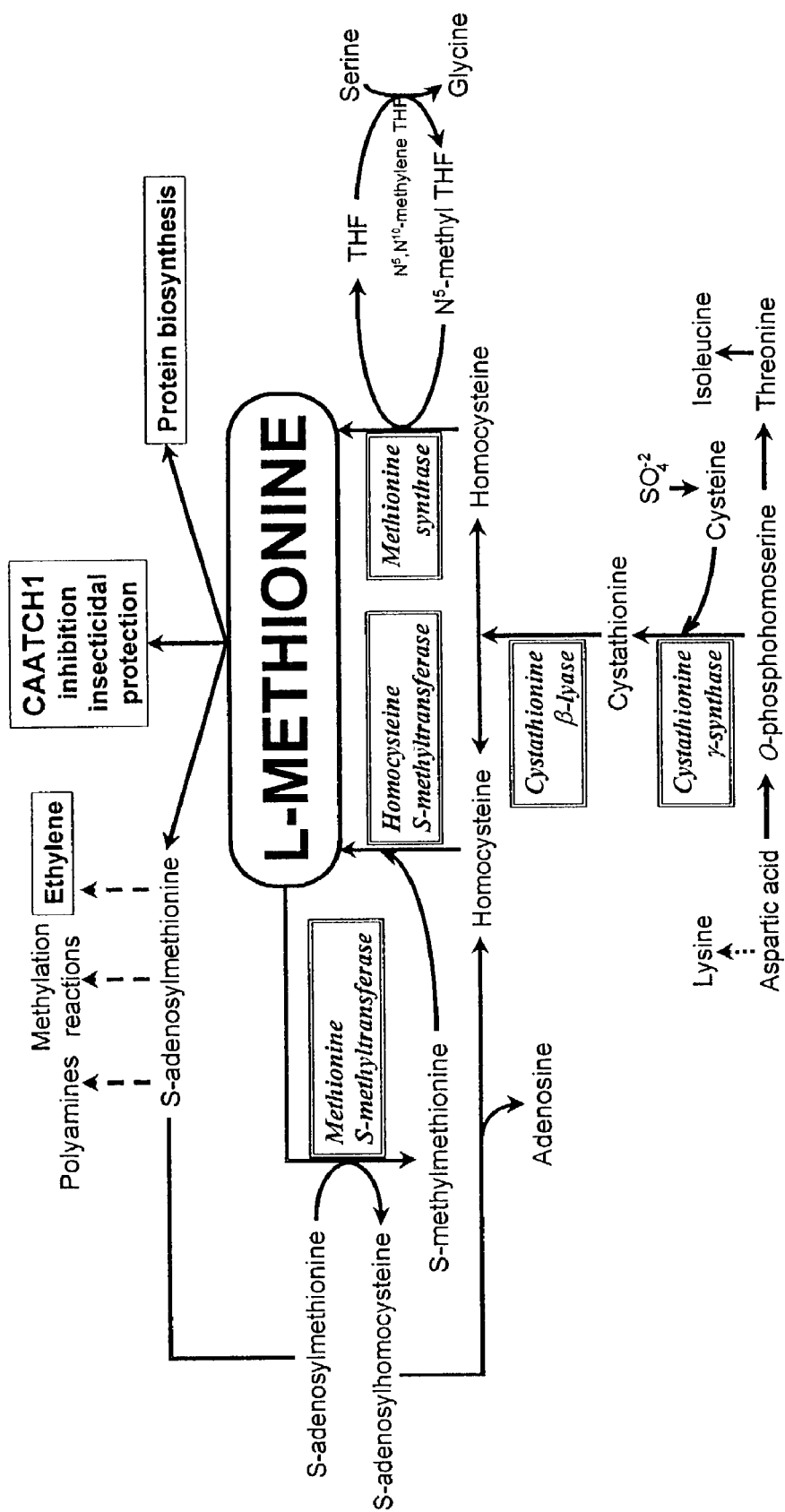
FIG. 9 shows examples of metabolic pathways leading to methionine biosynthesis or overproduction in typical higher plants.

A further aspect of the subject invention is the manipulation of metabolic pathways in plants that lead to biosynthesis of L-methionine, and/or pesticidal amino acids, and/or their analogs. Such manipulation in plants includes, but is not limited to, genes of the major metabolic pathways (FIG. 9) involving the enzymes cystathionine γ-synthase, cystathionine β-lyase, and methionine synthase. The subject invention also includes means to enhance sulfur assimilation in plants or other hosts via genes encoding, for example, ATP-sulfurylase, cysteine synthease, and serine acetyltransferase. Furthermore, another aspect of the subject invention includes means to enhance sulfur assimilation in plants or other pest hosts, including chemical presursors of pesticidal amino acids and their analogs added to soil amendments and plant fertilizers, or applied to plants by any means.

Definitions

As used herein, the term "pesticidal" refers to the ability to interfere with a pest's life cycle in any way that results in an overall reduction in the pest population. For example, the term pesticidal includes inhibition of a pest from progressing from one form to a more mature form, e.g., transition between various larval instars or transition from larva to pupa or pupa to adult. Further, the term "pesticidal" is intended to encompass anti-pest activity during all phases of a pest's life cycle; thus, for example, the term includes larvacidal, ovicidal, and adulticidal activity. As used herein, the term "pesticidally effective" is used to indicate an amount or concentration of a pesticidal compound which is sufficient to reduce the number of pests in a geographic locus as compared to a corresponding geographic locus in the absence of the amount or concentration of the pesticidal compound. Pests which can be controlled according to the subject invention are invertebrate animal pests of homes, people, and agriculture. "Pest Control" as used herein includes "pesticidal" activity as well as pest aversion activity which causes a pest to avoid deleterious behavior such as a mosquito biting, or a caterpillar eating an agricultural crop.

The word "transform" is broadly used herein to refer to introduction of an exogenous polynucleotide sequence into a prokaryotic or eukaryotic cell by any means known in the art (including for example, direct transmission of a polynucleotide sequence from a cell or virus particle, transmission by infective virus particles and transmission by any other nucleotide-bearing construct) resulting in a permanent or temporary alteration of genotype.

The term "upstream" refers to DNA adjacent to the 5' portion of a DNA sequence; whereas, the term "downstream" refers to DNA adjacent to the 3' portion of a DNA sequence.

A "transgenic cell" is any cell derived or regenerated from a transformed cell or derived from a transgenic cell. Exemplary transgenic cells include plant calli derived from a transformed plant cell and particular cells such as leaf, root, stem, e.g., somatic cells, or reproductive (germ) cells obtained from a transgenic plant.

As used herein, a "transgenic plant" is a plant or progeny thereof derived from a transformed plant cell or protoplast, wherein the plant DNA contains an introduced exogenous DNA molecule not originally present in a native, non-transgenic plant of the same strain.

In accordance with the present invention, nucleic acid sequences include and are not limited to, DNA, including and not limited to cDNA and genomic DNA, and genes; RNA, including and not limited to mRNA and tRNA; antisense sequences; and recombinant vectors, including, for example, plasmids, cosmids, phagemids, artificial chromosomes, phage, viruses, baculoviruses, and the like.

The term "gene" is used for simplicity to refer to a functional protein-, polypeptide- or peptide-encoding unit. As will be understood by those in the art, this functional term includes genomic sequences, operon sequences and smaller engineered gene segments that express, or may be adapted to express, proteins, polypeptides or peptides.

As used herein with regard to molecular biology, a "vector" is a DNA molecule capable of replication in a host cell and/or to which another DNA segment can be operatively linked so as to bring about replication of the attached segment. A plasmid is an exemplary vector. Note, however, that in entomology terms, a "vector" is a disease transmitting insect.

The terms "polypeptide", "peptide", and "protein" as used herein refer to amino acid sequences of two or more amino acids.

The term "monomer" is used to describe a single polypeptide. A monomer may exhibit physiological, biochemical, and/or insecticidal activity by itself, or may require the presence of another polypeptide to manifest these functions.

The term "subunit" or "ancillary polypeptide" is used to denote a polypeptide or protein that, in conjunction with another polypeptide, is required for physiological activity. The subunit or ancillary polypeptide may be associated with another polypeptide by covalent bonds, electrostatic interactions, or by hydrophobic interactions. Alternatively, the subunit or ancillary polypeptide may not exhibit any direct linkage with another polypeptide, yet is required for manifesting physiological or pesticidal activity of polypeptide(s). Alternatively, the subunit or ancillary polypeptide my aid in cellular/membrane trafficking of other polypeptides associated with solute transporter/ion channel activity.

The terms "multimer" or "multimeric" are used to denote an entity comprised of more than one polypeptide. The multimer could be comprised of the same polypeptide (e.g., two such polypeptides would comprise a homodimer) or different polypeptides (e.g., two different polypeptides would comprise a heterodimer). The components of the multimer may be associated with one another by covalent bonds, electrostatic interactions, or by hydrophobic interactions. Alternatively, the components of the multimer may not exhibit any direct linkage with another polypeptide, yet are required for manifesting physiological or pesticidal activity of polypeptide(s).

The one-letter symbol for the amino acids used herein is well known in the art. For convenience, the relationship of the three-letter abbreviation and the one-letter symbol for amino acids is as follows:

| | |
|---|---|
| Ala | A |
| Arg | R |
| Asn | N |
| Asp | D |
| Cys | C |
| Gln | Q |
| Glu | E |
| Gly | G |
| His | H |
| Ile | I |
| Leu | L |
| Lys | K |
| Met | M |
| Phe | F |
| Pro | P |
| Ser | S |

-continued

| | |
|---|---|
| Thr | T |
| Trp | W |
| Tyr | Y |
| Val | V |

CAATCH 1

In a preferred embodiment, the subject invention provides materials and methods for achieving pest control by disrupting the function of the new class of transporter/channel proteins exemplified by the *Manduca sexta* CAATCH1 protein. The full length coding sequence of 2858 nucleotides (nt) contains an open reading frame of 1899 nt encoding a predicted 633 amino acid sequence. The nucleotide sequence of this CAATCH1 cDNA open reading frame is about 35–50% identical to a family of clones representing membrane transporters of neurotransmitters and amino acids in a number of species. The predicted amino acid sequence of this CAATCH1 protein is 35–40% identical to most of the stated transporters.

The most closely related clone appears to be the *Manduca sexta* KAAT1 leucine transporter (Castagna et al., 1998, *Proc. Natl. Acad. Sci. USA* 95:5395–5400), which is 92% identical overall with the CAATCH1 nucleotide sequence and 90% identical in the overall predicted amino acid sequence. Nonetheless, several regions yield conspicuous differences between CAATCH1 and KAAT1. Notably, the amino acid differences are particularly divergent within or near predicted transmembrane domains #6, #11 and #12, and their adjacent hydrophilic cytosolic C- and N-terminal regions. For example, within residues 496–577, 25 amino acids (or 31%) diverge.

Although the nucleotide and polypeptide sequences of KAAT1 and CAATCH1 are related, their notable differences are manifested in their striking physiological/functional differences. Thus, the structural and functional differences distinguish them as unique entities.

The DNA sequence information provided herein facilitates the preparation of DNA (or RNA) sequences having the ability to specifically hybridize to nucleic acid sequences encoding portions of the *Manduca sexta* CAATCH1 gene, and related genes. The ability of such nucleic acid probes to specifically hybridize to the corresponding CAATCH nucleic acid sequences lend them particular utility in the identification, isolation, and/or characterization of related genes and proteins. Such related proteins may be obtained from *Manduca sexta*, other members of the genus *Manduca*, *Aedes aegypti* and other mosquitoes, *Leptinotarsa decemlineata*, other insects, or from virtually any other source, plant, animal, fungal, or microbial, from which amino acid transporter/ion channel polypeptides may be isolated that show similarity or homology to the CAATCH polypeptide isolated from *Manduca sexta*, *Aedes aegypti*, or *Leptinotarsa decemlineata*, or which display similar physiological or functional traits in common with CAATCH1 either in situ in the insect or as expressed in vitro or in vivo.

Pesticidal Compositions and Methods of Use

The subject invention provides novel pest control compositions, and methods for using such compositions. In an embodiment that is preferred because of its effectiveness, simplicity, and eco-friendliness, a compound, which disrupts the critical functions of transporter proteins, can be administered to a target pest. Specifically exemplified herein is the pesticidal use of leucine and methionine, and/or analogs thereof.

In one embodiment, the subject compositions can be used to control pests of agricultural crops. These pests, include, for example, coleopterans (beetles), lepidopterans (caterpillars), mites, and nematodes. The Coleopterans include numerous beetle species including ground beetles, reticulated beetles, skin and larder beetles, long-horned beetles, leaf beetles, weevils, bark beetles, ladybird beetles, soldier beetles, stag beetles, water scavenger beetles, and a host of other beetles.

Particularly important among the Coleoptera are the agricultural pests included within the infraorders Chrysomeliformia and Cucujiformia. Members of the infraorder Chrysomeliformia, including the leaf beetles (Chrysomelidae) and the weevils (Curculionidae), are particularly problematic to agriculture, and are responsible for a variety of insect damage to crops and plants. The infraorder Cucujiformia includes the families Coccinellidae, Cucujidae, Lagridae, Meloidae, Rhipiphoridae, and Tenebrionidae. Within this infraorder, members of the family Chrysomelidae (which includes the genera *Exema*, *Chrysomela*, *Oreina*, *Chrysolina*, *Leptinotarsa*, *Gonioctena*, *Oulema*, *Monozia*, *Ophraella*, *Cerotoma*, *Diabrotica*, and *Lachnaia*), are well-known for their potential to destroy agricultural crops.

The compositions of the subject invention can be used as pesticidal formulations against members of the Order Lepidoptera. Likewise, the materials and methods of the subject invention can be used to control mosquitoes (including those in the genera *Aedes*, *Anopheles*, and *Culex*).

Crops which can be protected according to the subject invention as well as pests of these crops include those which are listed in published PCT Application Nos. WO 98/44137 and WO 96/10083 which are both incorporated herein by reference.

In a preferred embodiment, the pests controlled according to the subject invention have an alkaline gut compartment. As used herein, reference to alkaline gut compartment means that the typical pH of the gut compartment is greater than 7.0. The alkaline midgut of *Manduca sexta* is an example of such an alkaline gut compartment. Other pests having an alkaline gut compartment are set forth in Example 16. Further pest targets according to the subject invention include pests which have a V-type ATPase either expressed as a protein, mRNA, or genomic DNA.

Thus, amino acid-rich compositions, and particularly those that include methionine or leucine (or analogs thereof) in their formulation can be used as pesticides for application to field crops, including but not limited to rice, wheat, alfalfa, corn (maize), soybeans, tobacco, tomato, potato, eggplant, barley, canola (rapeseed), sugarbeet, sugarcane, flax, rye, oats, cotton, sunflower; grasses, such as pasture and turf grasses; fruits, citrus, nuts, trees, shrubs and vegetables; as well as ornamental plants, cacti, succulents, and the like. Preferred embodiments include plants selected from the group consisting of maize, sorghum, wheat, sunflower, tomato, cole crops, cotton, rice, soybean, sugar beet, sugarcane, tobacco, barley, and oilseed rape. In a particularly preferred embodiment, the plant is a maize plant.

Additional target crops to be protected within the scope of the present invention comprise, e.g., the following species of plants:

Cereals (wheat, barley, rye, oats, rice, sorghum and related crops), beet (sugar beet and fodder beet), forage grasses (orchard grass, fescue, and the like), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fiber plants (cotton, flax, hemp, jute), citrus fruit (oranges, lemons, grapefruit, mandarins), vegetables (spinach, lettuce, asparagus, cabbages and other Brassicae, onions, tomatoes, potatoes, paprika), lauraceae (avocados, carrots, cinnamon, camphor), deciduous trees and conifers (e.g. linden-trees, yew-trees, oak-trees, alders, poplars, birch-trees, firs, larches, pines), or plants such as maize, tobacco, nuts, coffee, sugar cane, tea, vines, hops, bananas and natural rubber plants, as well as ornamentals (including composites).

Pesticidal compounds of the subject invention can be used, alone or in combination with other pesticides, to control one or more non-mammalian pests. These pests may be, for example, those listed in Table 1. Activity can readily be confirmed using the bioassays provided herein, adaptations of these bioassays, and/or other bioassays well known to those skilled in the art.

TABLE 1

Examples of Target pest species

| ORDER/Common Name | Latin Name |
|---|---|
| LEPIDOPTERA | |
| European Corn Borer | *Ostrinia nubilalis* |
| European Corn Borer resistant to Cry1 A | *Ostrinia nubilalis* |
| Black Cutworm | *Agrotis ipsilon* |
| Fall Armyworm | *Spodoptera frugiperda* |
| Southwestern Corn Borer | *Diatraea grandiosella* |
| Corn Earworm/Bollworm | *Helicoverpa zea* |
| Tobacco Budworm | *Heliothis virescens* |
| Tobacco Budworm Rs | *Heliothis virescens* |
| Sunflower Head Moth | *Homeosoma ellectellum* |
| Banded Sunflower Moth | *Cochylis hospes* |
| Argentine Looper | *Rachiplusia nu* |
| Cabbage Looper | *Trichopluia niI* |
| Spilosoma | *Spilosoma virginica* |
| Bertha Armyworm | *Mamestra configurata* |
| Diamondback Moth | *Plutella xylostells* |
| Red-banded Leaf Roller | *Argyrotaenia velutinana* |
| COLEOPTERA | |
| Red Sunflower Seed Weevil | *Smicronyx fulvus* |
| Sunflower Stem Weevil | *Cylindrocopturus adspersus* |
| Sunflower Beetle | *Zygoramma exclamationis* |
| Canola Flea Beetle | *Phyllotreta cruciferae* |
| Western Corn Rootworm | *Diabrotica virgifera virgifera* |
| Southern Pine Beetle | *Dendroctonus frontalis* |
| BLATTARIA | |
| Cockroach | *Periplaneta american* |
| DIPTERA | |
| Black Fly | *Simulium vittatum Zetterstedt* |
| | *Simulium venustum Say* |
| | *Simulium jenningsi* |
| | *Prosimulium sp* |
| Mosquito | *Culex, Anopheles, Aedes* spp. |
| Hessian Fly | *Mayetiola destructor* |
| Housefly | *Musca domestica* |
| HOMOPTERA | |
| Greenbug | *Schizaphis graminum* |
| ISOPTERA | |
| Termite | *Coptotermes formosanus* |
| HEMIPTERA | |
| Lygus Bug | *Lygus lineolaris* |
| NEMATODA | *Heterodera glycines* |

The pesticidal compounds of the present invention may be provided in a variety of ways. In one example the compounds are provided as a polypeptide, the amino acid sequence of which includes one or more pesticidal amino acids of the present invention. In various embodiments, two or more of the pesticidal amino acids are linked, for example, by peptide bonds between the N-terminus of one portion and the C-terminus of another portion. In other aspects, one or more of the pesticidal polypeptides can be linked to one or more heterologous peptides or proteins to form pesticidal fusion polypeptides. Molecules comprising such portions linked by hydrocarbon linkages are also provided. Derivatives of the foregoing fusion proteins are also provided (e.g., branched, cyclized, or C-terminal chemically modified, etc.).

Virtually any polypeptide-encoding DNA sequence may be fused to the sequences disclosed herein in order to encode a fusion protein. This includes DNA sequences that encode targeting peptides, proteins for recombinant expression, proteins to which one or more targeting peptides are attached, protein subunits, and the like. Such modifications to primary nucleotide sequences to enhance, target, or optimize expression of the gene sequence in a particular host cell, tissue, or cellular localization, are well known to those of skill in the art of protein engineering and molecular biology. Both N-terminal and C-terminal fusion proteins are contemplated.

Derivation of the pesticidal compounds with long chain hydrocarbons will facilitate passage through the cuticle into the pest body cavity. Therefore, in a further embodiment, the subject invention provides compositions comprising the pesticidal compounds bound to lipids or other carriers.

In addition to the peptide compounds described herein, the subject invention also contemplates that other sterically similar analog compounds may be formulated to mimic the key portions of the peptide structure. Such compounds, which may be termed peptidomimetics, may be used in the same manner as the peptides of the invention and hence are also functional equivalents. The generation of a structural functional equivalent analog may be achieved by the techniques of modeling and chemical design known to those of skill in the art. It will be understood that all such sterically similar analog constructs fall within the scope of the present invention.

The subject invention further contemplates the use of peptide nucleic acids (PNAs) in the practice of the methods of the invention. PNA is a DNA mimic in which the nucleobases are attached to a pseudopeptide backbone. PNA may be utilized in a number of methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (Corey, D. R. 1997, *Trends Biotechnol.* 15:224–229) and is incorporated herein by reference.

Any formulation methods known to those of skill in the art may be employed using methionine or leucine (or other pesticidal compounds as described herein) as an active ingredient. It may be desirable to formulate the amino acid composition alone, or alternatively, by addition of the methionine or leucine composition to existing pesticidal preparations for a combination or synergistic approach to eradicating target pests. For example, methionine or leucine can be added to whole cell preparations, cell extracts, cell suspensions, cell homogenates, cell lysates, cell supernatants, cell filtrates, or cell pellets of cell cultures of pesticide-producing microorganisms. In particular, it may be desired to supplement bacterial cell cultures such as those of *B. thuringiensis* that express one or more δ-endotoxins. The methods for preparing such formulations are known to those of skill in the art, and include, e.g., desiccation, lyophilization, homogenization, extraction, filtration, encapsulation centrifugation, sedimentation, or concentration of one or more cultures of bacterial cells, such as *B. thuringiensis* cells.

In one embodiment, the pesticide composition comprises an oil flowable suspension comprising a methionine or leucine composition. For example, in some embodiments, oil flowable or aqueous solutions may be formulated to contain lysed or unlysed bacterial cells, spores, or crystals which contain one or more pesticidally-active crystal proteins in combination with a methionine or leucine composition. Preferably the cells that contain the crystal protein component of the formulation are *B. thuringiensis* cells; however, any such bacterial host cell expressing one or more crystal-protein encoding polynucleotides is contemplated to be useful, such as *Bacillus* spp., including *B. megaterium, B. subtilis; B. cereus, Escherichia* spp., including *E. coli*, and/or *Pseudomonas* spp., including *P. cepacia, P. aeruginosa*, and *P. fluorescens*.

In a further embodiment, the pesticide may be formulated as a water dispersible granule or powder. This granule or powder may comprise one or more amino acids, and particularly, the amino acid methionine or leucine (or analogs thereof).

The pesticide compositions of the present invention may also comprise a wettable powder, spray, emulsion, colloid, aqueous or organic solution, dust, pellet, or colloidal concentrate. Dry forms of the pesticidal compositions may be formulated to dissolve immediately upon wetting, or alternatively, dissolve in a controlled-release, sustained-release, or other time-dependent manner.

Alternatively, the pesticidal composition may comprise an aqueous solution. Such aqueous solutions or suspensions may be provided as a concentrated stock solution which is diluted prior to application, or alternatively, as a diluted solution ready-to-apply. Such compositions may be formulated in a variety of ways. They may be employed as wettable powders, granules or dusts, by mixing with various inert materials, such as inorganic minerals (silicone or silicon derivatives, phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be employed as foams, suspensions, emulsifiable concentrates, or the like. The ingredients may include rheological agents, surfactants, emulsifiers, dispersants, or polymers.

The compositions may be formulated prior to administration in an appropriate means such as lyophilized, freeze-dried, microencapsulated, desiccated, or in an aqueous carrier, medium or suitable diluent, such as saline or other buffer. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in pesticide formulation technology.

The pesticidal compositions of this invention can be applied to the environment of the target pest, typically onto the foliage of the plant or crop to be protected, by conventional methods such as spraying. Other application techniques, e.g., dusting, sprinkling, soaking, soil injection, soil tilling, seed coating, seedling coating, spraying, aerating, misting, atomizing, and the like, are also feasible and may be required under certain circumstances such as e.g., pests that cause root or stalk infestation, or for application to delicate vegetation or ornamental plants. These application procedures are also well known to those of skill in the art.

To control mosquito larvae, the compositions may be applied to standing water. In this context, the composition may be, for example, a yeast or algae (or other mosquito or mosquito larvae food) which has been mixed with, or transformed to express, a pesticidal compound of the subject invention.

In the case of termites, the pesticidal compounds (such as methionine) can be used to form a barrier or, preferably are incorporated into a food source such as a wood article. The food source could be used, for example, as the toxicant in a Sentricon™ system.

The pesticidal compositions of the invention may be employed in the method of the invention singly or in combination with other compounds, including, but not limited to, other pesticides.

Regardless of the method of application, the amount of the active component(s) are applied at a pesticidially-effective amount, which will vary depending on factors such as, for example, the specific pests to be controlled, the specific plant or crop to be treated, the environmental conditions, and the method, rate, and quantity of application of the pesticidally-active composition.

The concentration of pesticidal composition that is used for environmental, systemic, or foliar application will vary widely depending upon the nature of the particular formulation, means of application, environmental conditions, and degree of biocidal activity. Typically, the composition will be present in the applied formulation at a concentration that provides the amino acid composition to the pest in a range of from about 0.1% by weight up to and including about 99% by weight. Formulations of the compositions may be from about 0.01% to about 1% by weight, or from 1% to about 75% or more by weight, with some formulations generally comprising from about 5% to about 50% or more of the active ingredient by weight. Formulations which comprise intact bacterial cells will generally contain from about $10^4$ to about $10^{12}$ cells/mg of the final formulation. The pesticidal formulation may be administered to a particular plant or target area in one or more applications as needed, with a typical field application rate per hectare ranging on the order of from about 1 g to about 5 kg, or more of active ingredient.

Transformed Host Cells and Transgenic Plants

A preferred embodiment of the subject invention provides transformed host cells and transgenic plants that express amino acids at levels that are pesticidal to pests feeding on such cells or plants. In a specific embodiment, methionine-encoding polynucleotides are introduced into cells to increase, alter, or affect the overall concentration of methionine within the cells. The recombinant host may be, for example, prokaryotic or eukaryotic cells such as yeast or algae. The transformed hosts can be applied to pest habitats, such as bodies of water inhabited by mosquito larvae. Ingestion of the transformed host by a pest species would lead to control of the pest by the pesticidal polypeptide.

Technology for introduction of polynucleotides into cells is well known to those of skill in the art. Four general methods for delivering a gene into cells have been described: (1) chemical methods; (2) physical methods such as microinjection, electroporation and the gene gun; (3) viral vectors; and (4) receptor-mediated mechanisms. Methods for DNA transformation of plant cells include *Agrobacterium*-mediated plant transformation, protoplast transformation, gene transfer into pollen, injection into reproductive organs, injection into immature embryos and particle bombardment.

Bacteria, yeasts, algae, plants, and viruses (including virus particles) each may be used in the production of pesticidal polypeptides for further use, or these hosts can be used as vehicles for direct application of pesticidal polypeptides to the target pest. Plants can be transformed to render them toxic to a target pest species that feeds on the transformed plant. In this way, the plant may also be rendered undesirable as a food source thus reducing damage to the plant.

Typically, a gene of interest is introduced between the transcriptional and translational initiation region and the transcriptional and translational termination region, so as to be under the regulatory control of the initiation region. This construct is included in a plasmid, which includes at least one replication system. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Hosts of particular interest are the prokaryotes and the lower eukaryotes, such as fungi. Illustrative prokaryotes, both Gram-negative and gram-positive, include Enterobacteriaceae; Bacillaceae; Rhizobiceae; Spirillaceae; Lactobacillaceae; and phylloplane organisms such as members of the Pseudomonadaceae. Particularly preferred host cells include *Pseudomonas aeruginosa*, *Pseudomonas fluorescens*, *Bacillus thuringiensis*, *Escherichia coli*, *Bacillus subtilis*, and the like.

Among eukaryotes are fungi, such as *Phycomycetes* and *Ascomycetes*, which includes yeast, such as *Schizosaccharomyces*; and *Basidiomycetes*, *Rhodotorula*, *Aureobasidium*, *Sporobolomyces*, *Saccharomyces* spp., and *Sporobolomyces* spp.

A large number of cloning vectors are available for the insertion of foreign genes into many organisms, including plants. In some instances, it may be desirable to provide for regulative expression of the gene encoding the gene of interest where expression is regulated by certain cellular stimuli, environmental conditions, cell cycle, or other inductive or repressive factor(s). This can be achieved, for example, through the incorporation of one or more operators, enhancers, or a region of DNA that binds to an activator or an enhancer, into the genetic element that comprises the gene, so that the genetic construct may be expressed under certain controlled conditions.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the $\lambda_L$ and $\lambda_R$ promoters, the tac promoter, the naturally-occurring promoters associated with the transport protein-encoding gene, where functional in the host. See for example, U.S. Pat. Nos. 4,332,898; 4,342,832; and 4,356,270 (each of which is specifically incorporated herein by reference).

Where stable episomal maintenance or integration is desired, a plasmid will be employed which has a replication system that is functional in the host. A large number of plasmids are available, such as pBR322, pACYC184, RSF1010, pRO1614, and the like. See for example, U.S. Pat. Nos. 4,356,270; 4,362,817; 4,371,625, and 5,441,884, each incorporated specifically herein by reference.

In other embodiments, it is contemplated that certain advantages will be gained by positioning the coding DNA segment under the control of a recombinant, or heterologous, promoter. The use of promoter and cell type combinations for protein expression is generally known to those of skill in the art of molecular biology, for example, see Maniatis et al. (Sambrook, J., E. F. Fritsch and T. Maniatis, 1989, *Molecular Cloning: A Laboratory Manuel*, Cold Spring Harbor Laboratory, New York). The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the *Pichia* expression vector system (Pharmacia LKB Biotechnology).

Following are examples that illustrate procedures for practicing the invention. These examples should not be construed as limiting. All percentages are by weight and all solvent mixture proportions are by volume unless otherwise noted.

EXAMPLE 1

Cloning and Characterization of a Ligand-Gated Ion Channel/Amino Acid Transporter A full-length clone was isolated from a midgut cDNA library (in LambdaZap) derived from the fifth instar larval stage of *Manduca sexta*. The clone included 5' and 3' untranslated regions, in addition to a functional open reading frame. A strategy was employed using inosine degenerate primer touchdown PCR™ combined with specific primer based PCR™ screening of phage lysates to isolate the clone (denoted "CAATCH1"), with subsequent expression and extensive in vitro characterization of the expressed polypeptide product in membranes of *Xenopus oocytes*.

An initial set of inosine ("I")-containing degenerate primers was designed (Feldman et al. 2000, *J. Biol. Chem.* 275:24518–24526) to target conserved peptide motifs from invertebrate and vertebrate members of a subfamily of Na/Cl dependent transporters serving various neurotransmitters and amino acids (Griffith, J. K. and C. E. Sansom 1998 In: The Trasnporter Facts Book, Academic Press, San Diego, pp. 500). All primers are shown in the 5' to 3' direction. The sense primer "S34" (GGIAA(C/T)GTITGG(A/C)G(A/G/C/T)TT(C/T)CC) (SEQ ID NO:3) was based on a GNVWRFP (SEQ ID NO:4) peptide motif, while the antisense primer "S21" (IGC(A/G/T)ATIGCITC(A/G/C/T)GG(A/G)TA) (SEQ ID NO:5) was based on a YP(D/E)AIA (SEQ ID NO:6) peptide motif. Another sense primer "S22" (GGIAA(C/T)GTITGG(G/T)G(A/G/C/T)TT(C/T)CC) (SEQ ID NO:7), a tolerated alternative to S34, was also used in conjunction with S21 antisense primer for initial screening. Another primer set was designed to specifically exclude KAAT1 and other potentially related sequences, including, while amplifying a unique 328 bp segment. In this case, sense primer "S25" (AACACTTGCTGCATCAGTCAAC) (SEQ ID NO:8) and antisense primer "S26" (CTCAAGGAGTTTCGCCCATTG) (SEQ ID NO:9). The S25/S26 set was used for subsequent library phage lysate PCR™ screening steps, and was used with the cloned 943 bp fragment to create a 328 bp digoxigenin (DIG)-labeled (Boehringer-Mannhiem) dsDNA plaque hybridization probe for the isolation of a single clone. The sequence of the full length clone (SEQ ID NO:1) was determined, including the open reading frame plus the 3' and 5' untranslated regions.

EXAMPLE 2

Cloning and Characterization of a Ligand-Gated Ion Channel/Amino Acid Transporter A CAATCH1 gene, and other genes encoding transporter/channel proteins, or regulatory subunits, or polypeptide members of multimeric systems, can also be cloned from mRNA. In this case, the RNA is isolated from excised larval guts, intact larvae, or from any animal organism at any stage of development. First strand cDNA is produced using reverse transcriptase with either primer "AP" (Gibco Life Technologies) (GGCCACGCGTCGACTAG-TACTTTTTTTTTTTTTTTT) (SEQ ID NO:10), or PA142_AP"(GACTTCAGGCTAGCATCGATC-CATGGGTCGACTTTTTTTTTTTTTTTT) (SEQ ID NO:11). CAATCH1-specific fragments are subsequently amplified from the first strand cDNA by PCR™ using a proofreading DNA polymerase mixed with Taq (Invitrogen; Platinum HighFidelity), employing various primer combinations of sense and antisense sequences.

Examples of sense sequences that can be used to clone and/or sequence CAATCH1 includes the following (all shown in the 5' to 3' direction):

| Name | Sequence | SEQ ID |
|---|---|---|
| "PA140_AUAP" | (GACTTCAGGCTAGCATCGATCCA); | (SEQ ID NO:12) |
| "PA141" | (CATCGATCCATGGGTCGAC); | (SEQ ID NO:13) |
| "AUAP (Gibco)" | (GGCCACGCGTCGACTAGTAC); | (SEQ ID NO:14) |
| "left1_Forward" | (GGCACGAGGTTACTTGTTGG); | (SEQ ID NO:15) |
| "left2_Forward" | (CGAGGTTACTTGTTGGAGGAA); | (SEQ ID NO:16) |
| "ATG1_Forward" | (TTGTGGACAAAATGAATGACG); | (SEQ ID NO:17) |
| "ATG2_Forward" | (AAAATGAATGACGGCCAAGT); | (SEQ ID NO:18) |
| "S25TrueFOR" | (AACACTTGCTGCATCAGTCAAC); | (SEQ ID NO:8) |
| "uniqueFOR" | (TGCTGCATCAGTCAACAACA); | (SEQ ID NO:19) |
| "TaqFOR" | (TCATCCTGCCCGGTGCTA); | (SEQ ID NO:20) |
| "1445_FOR" | (ACACCGGGTGGACAATATATTCTT); | (SEQ ID NO:21) |
| "StopORF_FOR" | (GGTGCTTACAGGCGTAATATTAATTAG); | (SEQ ID NO:22) |
| "3'UTR_FOR" | (CGGTGTCGATATTATACATGTTACGA) and | (SEQ ID NO:23) |
| "S34" | (GGIAA(C/T)GTITGG(A/C)G(A/G/C/T)TT(C/T)CC). | (SEQ ID NO:3) |

Examples of antisense sequences that can be used to clone and/or sequence CAATCH1 includes (all shown from 5' to 3' direction):

| Name | Sequence | SEQ ID |
|---|---|---|
| "CAATCH1_unique REVERSE" | (AGGAGTTTCGCCCATTGAG); | (SEQ ID NO:24) |
| "Taq_CAATCH1_REVERSE" | (CAAGGAGTTTCGCCCATTGA); | (SEQ ID NO:25) |
| "S26_REVERSE" | (CTCAAGGAGTTTCGCCCATTG); | (SEQ ID NO:9) |
| "CAATCH1_2642 REV" | (CTATAAAATCAAACGCAAGACCAT); and | (SEQ ID NO:26) |
| CAATCH1_2727_REV" | (TGTTGCACAGAGTTCTTGAAGATTT). | (SEQ ID NO:27) |

EXAMPLE 3

DNA Sequence Analysis and Protein Functional Behavior

The complete sequence of the CAATCH1 cDNA clone, including 5' and 3' UTRs and the open reading frame encoding the predicted 633 amino acid polypeptide expression product, were obtained for *Manduca sexta* using a midgut cDNA library in LambdaZap phage. The *Manduca* CAATCH1 Genbank accession No. is AF013963 (SEQ ID NO:1).

The CAATCH1 nucleotide coding sequence within the full length clone of 2858 nt (SEQ ID NO:1) contained an open reading frame encoding a predicted unique polypeptide sequence of 633 amino acids (SEQ ID NO:2). The predicted amino acid sequence of CAATCH1 is compared to related members of a subfamily of membrane proteins that includes Na/Cl activated transporters of neurotransmitters (Quick, M. and B. R. Stevens, 2001, *J. Biol. Chem.* 276(36):33413–33418; Feldman et al, 2000, *J. Biol. Chem.* 275(32):24518–24526; Griffith, J. K. and C. E. Sansom, 1998, In: The Transporter Facts Book, Academic Press, San Diego, pp. 500) and the *Manduca* KAAT1 leucine transporter (Castagna et al., 1998, *Proc. Natl. Acad. Sci. USA* 95:5395–5400). Based on hydropathy analysis and established membrane protein structure paradigms (Kyte and Doolittle, 1982, *J. Mol. Biol.* 157:105–132), the predicted CAATCH1 protein topology includes 12 putative transmembrane domains, with N- and C-terminal segments residing within the cytosol. Several consensus phosphorylation sites are found within these cytoplasmic segments, and N-linked glycosylation sites exist on the putative extracellular loop between the 3rd and 4th membrane spanning segments. The cytosolic N- and C-terminal regions are relatively rich in proline, acidic, and basic amino residues.

Membrane transporters and ion channels in general can be subcategorized based on thermodynamic properties, substrate selectivities, reaction mechanism, and multimeric/monomeric relationship of polypeptides (Gerencser, G. A. and B. R. Stevens, 1994, *J. Exper. Biol.* 196:59–75; Hille, B., 2001, In: Ion Channels of Excitable Membranes, 3$^{rd}$ Edition, Sinauer Associates, Inc., Sunderland, Mass, pp 814; Saier, M. H., 2000, Families of proteins forming transmembrane channels. *J. Membrane Biol.* 175:165–180; Saier, M. H., 2000, A functional-phylogenetic classification system for transmembrane solute transporters, *Micro. Molec. Biol. Rev* 64:354–411; Verrey, F., Jack, D. L., Paulsen, I. T., Saier, M. H., and Pfeiffer, R., 1999, New glycoprotein-associated amino acid transporters, *J. Membrane Biol.,* 172:181–192; Saier, M. H., 2000, Families of transmembrane transporters selective for amino acids and their derivatives, *Microbiology*, 146:1775–1795; Wagner, C. A., Lang, F., and Broer, S., 2001, Function and structure of heterodimeric amino acid transporters, *Am. J. Physiol. Cell Physiol,.* 281:C1077–C1093; Kanai, Y., and Endou, H., 2001, Heterodimeric amino acid transporters: molecular biology and pathological and pharmcological relevance, *Curr. Drug Metabol.,* 2:339–354.

CAATCH1 cloned from *Manduca sexta* displays a unique set of properties (Quick, M. and B. R. Stevens, 2001, supra; Feldman et al., 2000, supra) that have not been described previously for a given related transporter, including at least the following attributes. The attributes include: (a) the ability to switch particular amino acid substrate selectivities depending on the activator cation $Na^+$ or $K^+$, (b) a unique selectivity profile of amino acid-evoked electrical currents, (c) different amino acid substrates directly binding the protein and differentially affecting the conformational states of CAATCH1, apparent lack of chloride ion as a co-activator, (d) Nernstian cation channel behavior independent of amino acid transporter activity, (e) amino acid-modulated ion channel behavior (especially L-methionine binding to CAATCH1 in the presence of $Na^+$ which perturbs the charge-voltage relation with a high affinity binding constant, affecting transient currents due to CAATCH1-associated charge transfer across the membrane dielectric field), (f) inhibition of current fluxes as the result of binding of methionine to the protein, (g) thermodynamically uncoupled amino acid transport and ion channel behavior, and (h) all these functions behave optimally at an alkaline pH.

CAATCH defines a new transport system (Quick, M. and B. R. Stevens, 2001, supra; Feldman et al., 2000, supra; Castagna et al., 1998, supra; Christensen, H. N. 1990, *Physiol. Rev.* 70:43–77; Griffith and Sansom, 1998, supra; Kilberg et al., 1993, *Annu. Rev. Nutr.* 13:137–165; Mailliard et al., 1995, *Gastroenterology* 108:888–910; Malandro and Kilberg, 1996; Stevens, B. R., 1992, "Amino Acid Transport in Intestine" In: Mammalian Amino Acid Transport: Mechanisms and Control, pp 149–164, M. S. Killberg and D. Haussinger, eds., Plenum, N.Y.). The transport of amino acids by CAATCH serves the simultaneous and independent roles of nutrient transporter and amino acid-gated ion channel in at least *Manduca sexta*.

EXAMPLE 4

Identifying CAATCH Proteins and their Genes, and/or Polypeptides Required for CAATCH Activity, and their Genes; as well as Similar Solute Transporter/Ion Channel Proteins and their Genes Homologous polynucleotides and polypeptides can be identified and obtained through several means. The specific genes, or portions thereof, may be constructed synthetically. Variations of these genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Also, genes that code for active fragments may be obtained using a variety of other restriction enzymes. Proteases may be used to directly obtain active fragments of these amino acid transport proteins.

Equivalent amino acid transporter/ion channel proteins and/or genes encoding these equivalent amino acid transport/ion channel proteins can also be isolated from, or identified in, other insects, or other species of mosquitoes, hornworms, or caterpillars and/or pest-specific DNA or RNA libraries. For example, antibodies to the amino acid transport proteins disclosed and claimed herein can be used to identify and isolate other amino acid transport proteins. Specifically, antibodies may be raised to the portions of the amino acid transport proteins that are most constant and most distinct from other proteins. These antibodies can then be used to specifically identify equivalent polypeptides with the characteristic transport activity by immunoprecipitation, enzyme linked immunoassay (ELISA), or Western blotting.

A further method for identifying the amino acid transporter/ion channel proteins and genes of the subject invention is through the use of oligonucleotide probes. These probes are nucleotide sequences having a detectable label.

As is well known in the art, if the probe molecule and nucleic acid sample hybridize by forming a strong bond between the two molecules, it can be reasonably assumed that the probe and sample share significant homology. The probe's detectable label provides a means for determining in a known manner whether hybridization has occurred. Such a probe analysis provides a rapid method for identifying, isolating, and/or characterizing amino acid transport protein-encoding genes of the subject invention.

The nucleic acid sequences provided herein have utility as probes or primers in nucleic acid hybridization embodiments. Such sequences may involve the purine and pyrimidine nucleotides and/or inosine substitutions, and may be arranged to encode amino acids according to sequences representing degeneracy of codon usage (Table 2). As such, it is contemplated that nucleic acid segments that comprise a sequence region that consists of at least about 15 nucleotide contiguous sequence that has the same sequence as, or is complementary to, a 15 nucleotide contiguous DNA segment of SEQ ID NO:1 will find particular utility. Longer contiguous identical or complementary sequences, e.g., those of about 20, 50, 100, 500, 1000, 5000, 10,000 etc. (including all intermediate lengths and up to and including full-length sequences) will also be of use in certain embodiments. The preferred nucleic acid sequence employed for hybridization studies or assays includes sequences that have, or are complementary to, at least an about 15 to about 29 nucleotide stretch of the sequence, although sequences of about 30 to about 50 nucleotides are also useful. In particular, such polynucleotides preferably comprise contiguous regions from SEQ ID NO:1, and hybridize to the sequence of SEQ ID NO:1 under high stringency hybridization conditions. A variety of hybridization techniques and systems are known that can be used in connection with the hybridization aspects of the invention, including diagnostic assays such as those described in U.S. Pat. No. 4,358,535, incorporated herein by reference.

TABLE 2

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | trp | W | UGG | | | | | |
| Tyrosine | Tyr | Y | UAC | UAU | | | | |

Various degrees of stringency of hybridization can be employed. The more severe the conditions, the greater the complementarity that is required for duplex formation. Temperature, probe concentration, probe length, ionic strength, time, and the like can control severity of conditions. Preferably, hybridization is conducted under moderate to high stringency conditions by techniques well known in the art, as described, for example, Keller, G. H., M. M. Manak, 1987, In: *DNA Probes*, Stockton Press, New York, N.Y., pp. 169–170.

Examples of various stringency conditions are provided herein. Hybridization of immobilized DNA on Southern blots with $^{32}$P-labeled gene-specific probes can be performed by standard methods (Sambrook et al., 1982, *Molecular Cloning: A Laboratory Manual*, Cold Spring Harbor Laboratory, New York.). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20–25° C. below the melting temperature ($T_m$) of the DNA hybrid in 6×SSPE, 5× Denhardt's solution, 0.1% SDS, 0.1 mg/ml denatured DNA. The melting temperature is described by the following formula (Beltz et al., 1983, *Methods of Enzymology*, 100: 266–285, R. Wu, L. Grossman and K. Moldave, eds., Academic Press, New York).

$T_m$=81.5 C+16.6 Log[Na+]+0.41(% G+C)−0.61(% formamide)−600/length of duplex in base pairs.

Washes are typically carried out as follows:

(1) twice at room temperature for 15 minutes in 1×SSPE, 0.1% SDS (low stringency wash);

(2) once at ($T_m$)−20° C. for 15 minutes in 0.2×SSPE, 0.1% SDS (moderate stringency wash).

For oligonucleotide probes, hybridization can be carried out overnight at 10–20° C. below the melting temperature ($T_m$) of the hybrid in 6×SSPE, 5× Denhardt's solution, 0.1% SDS, 0.1 mg/ml denatured DNA. Tm for oligonucleotide probes can be determined by the following formula:

$T_m$(C)=2(number T/A base pairs)+4(number G/C base pairs) (Suggs et al., 1981, *ICN-UCLA Symp. Dev. Biol. Using Purified Genes*, D. D. Brown, ed., Academic Press, New York, 23:683–693).

Washes can be carried out as follows:

(1) twice at room temperature for 15 minutes 1×SSPE, 0.1% SDS (low stringency wash;

(2) once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

| Low: | 1 or 2X SSPE, room temperature |
| Low: | 1 or 2X SSPE, 42° C. |
| Moderate: | 0.2X or 1X SSPE, 65° C. |
| High: | 0.1X SSPE, 65° C. |

Duplex formation and stability depend on substantial complementarity between the two strands of a hybrid and, as noted above, a certain degree of mismatch can be tolerated.

The ability of such nucleic acid probes to specifically hybridize to CAATCH1 protein-encoding sequences enable them to be of use in detecting the presence of complementary sequences in a given sample.

Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one would desire to employ varying conditions of hybridization to achieve varying degrees of selectivity of probe towards target sequence. For applications requiring high selectivity, one will typically desire to employ relatively high stringency conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating DNA segments encoding amino acid transport/ion channel proteins. Detection of DNA segments via hybridization is well known to those of skill in the art, and the teachings of U.S. Pat. Nos. 4,965,188 and 5,176,995 (each incorporated herein by reference) are exemplary of the methods of hybridization analyses.

For some applications, for example, where one desires to prepare mutants employing a mutant primer strand hybridized to an underlying template or where one seeks to isolate amino acid transporter/ion channel protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. In any case, it is generally appreciated that conditions can be rendered more stringent by the addition of increasing amounts of formamide, which serves to destabilize the hybrid duplex in the same manner as increased temperature.

In illustrative embodiments, the polynucleotides of the present invention may comprise a nucleic acid sequence having at least about 60% preferably more than about 70%, more preferably more than about 85%, even more preferably more than about 90%, most preferably more than about 95%, even up to and including about 96%, about 97%, about 98%, or about 99% or greater sequence identity with a contiguous nucleic acid sequence of at least about 15 or so nucleotides from SEQ ID NO:1. Of course, the percent identity to a contiguous nucleic acid sequence from SEQ ID NO:1 need not be limited to the specific percentages given, but is also meant to include all integers between about 60% and about 99% identity with a contiguous nucleic acid sequence of at least about 15 nucleotides from SEQ ID NO:1. In fact, all such sequences are contemplated to fall within the scope of the present invention, so long as the particular sequence retains the relevant function.

The CAATCH1 nucleotides and sequences of the present invention include those comprising the stated open reading frame, as well as the 3' and 5' untranslated regions of both the sense and antisense sequences. Furthermore, the polynucleotides of the present invention include all splice variants arising from one or more genomic DNA sequences. Furthermore, both the sense and anitisense versions of the primer sequences used to clone or sequence CAATCH1 nucleotide sequences are included in this invention.

EXAMPLE 5

Methods for Making and Using Antibodies

Antibodies, both polyclonal and monoclonal, specific for CAATCH1 and other CAATCH peptides and/or epitopes may be prepared using conventional immunization techniques. A composition containing antigenic CAATCH epitopes can be used to immunize one or more animals, such as a rabbit or mouse, which will then produce specific antibodies against epitope-containing CAATCH peptides. Polyclonal antisera may be obtained, after allowing time for antibody generation, simply by bleeding the animal and preparing serum samples from the whole blood.

One feature provided by the present invention is a polyclonal sera that is relatively homogenous with respect to the specificity of the antibodies therein. Typically, polyclonal antisera are derived from a variety of different "clones," i.e. B-cells of different lineage. Monoclonal antibodies, by contrast, are defined as coming from antibody-producing cells with a common B-cell ancestor, hence their "mono" clonality. mAbs may be readily prepared through use of well-known techniques, such as those exemplified in U.S. Pat. No. 4,196,265, incorporated herein by reference.

In general, both poly- and monoclonal antibodies against these peptides may be used in a variety of embodiments. For example, they may be employed in antibody cloning protocols to obtain cDNAs or genes encoding the peptides disclosed herein or related proteins. They may also be used to inhibit the effects of CAATCH in cells or animals.

EXAMPLE 6

Epitopic Core Sequences

The present invention also provides CAATCH polypeptide compositions, free from total cells and other polypeptides, which comprise a purified CAATCH polypeptide which incorporates an epitope that is immunologically cross-reactive with one or more of the CAATCH-specific antibodies of the present invention.

As used herein, the term "incorporating an epitope(s) that is immunologically cross-reactive with one or more anti-CAATCH antibodies" refers to an antigen which includes a primary, secondary or tertiary structure similar to an epitope located within a CAATCH polypeptide. The level of similarity will generally be to such a degree that monoclonal or polyclonal antibodies directed against the CAATCH polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

One may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences. The amino acid sequence of these "epitopic core sequences" may then be readily incorporated into peptides, either through the application of peptide synthesis or recombinant technology.

As an exemplary embodiment, to conduct a competition study between CAATCH1 and any test compound, one would first label CAATCH with a detectable label to enable subsequent identification. One would then incubate the labeled antigen with the other, test, antigen and, after mixing, one would then add the mixture to a known antibody. The ability of the mixture to bind to the antibody would be determined by detecting the presence of the specifically bound label. This value would then be compared to a control value in which no potentially competing (test) antigen was included in the incubation.

The assay may be any one of a range of immunological assays based upon hybridization, and the reactive antigens would be detected by means of detecting their label, e.g., using streptavidin in the case of biotinylated antigens or by using a chromogenic substrate in connection with an enzymatic label or by simply detecting a radioactive or fluorescent label.

A significant reduction in labeled antigen reactivity in the presence of a test antigen is indicative of a test antigen that is "cross-reactive", i.e. that has binding affinity for the same antibody. "A significant reduction", in terms of the present application, may be defined as a reproducible (i.e. consistently observed) reduction in binding.

EXAMPLE 7

Mutagenesis of CAATCH Polypeptides and Polynucleotides

In certain embodiments, it is desirable to prepare mutant polypeptides and/or polynucleotides that encode them. Once the structure of the desired peptide to be mutagenized has been analyzed, it may often be desirable to introduce one or more mutations into either the polypeptide sequence, alternatively, into the DNA sequence encoding the CAATCH-derived polypeptide for the purpose of producing a mutated peptide with altered biological properties.

To that end, the present invention encompasses both site-specific mutagenesis methods and random mutagenesis of a nucleic acid segment encoding a transport polypeptide of the present invention. Mutagenesis may be performed in accordance with any of the techniques known in the art such as and not limited to synthesizing an oligonucleotide having one or more mutations within the sequence of a particular polypeptide.

For example, certain amino acids may be substituted for other amino acids in a protein structure without appreciable loss of interactive binding capacity with structures such as, for example, antigen-binding regions of antibodies or binding sites on substrate molecules.

In making such changes, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

EXAMPLE 8

Pesticidal use of RNAi

One method for disrupting transporter/channel protein function according to the subject invention is by the use double-stranded interfering RNA (RNAi), or RNA-mediated interference (RNAi). When RNAi corresponding to a sense and antisense sequence of a target mRNA is introduced into a cell, the targeted mRNA is degraded and protein translation of that message is stopped. Although not yet fully understood, the mechanism of this post-transcriptional gene silencing appears to be at least partially due to the generation of small RNA molecules, about 21–25 nucleotides in length, that correspond to (preferably at least 90% identity) the sense and antisense pieces of the RNAi introduced into the cell (Bass, B. L., 2000 "Double-stranded RNA as a template for gene silencing" *Cell* 101:235–238). The specificity of this gene silencing mechanism is extremely high, blocking expression only of targeted genes, while leaving other genes unaffected (Chuang, C. -F. and E. M. Meyerowitz, 2000 "Specific and heritable genetic interference by double-stranded RNA in *Arabidopsis thaliana*" *Proc. Natl. Acad. Sci. USA* 97:4985–4990).

dsRNA (RNAi) typically comprises a polynucleotide sequence identical to a target gene (or fragment thereof) linked directly, or indirectly, to a polynucleotide sequence complementary to the sequence of the target gene (or fragment thereof). The dsRNA may comprise a polynucleotide linker (stuffer) sequence of sufficient length to allow for the two polynucleotide sequences to fold over and hybridize to each other; however, a linker sequence is not necessary. The linker (stuffer) sequence is designed to separate the antisense and sense strands of RNAi significantly enough to limit the effects of steric hindrances and allow for the formation of dsRNA molecules.

RNA containing a nucleotide sequence identical to a fragment of the target gene is preferred for inhibition; however, RNA sequences with insertions, deletions, and point mutations relative to the target sequence can also be used for inhibition. Sequence identity may optimized by sequence comparison and alignment algorithms known in the art (see Gribskov and Devereux, *Sequence Analysis Primer*, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Alternatively, the duplex region of the RNA may be defined functionally as a nucleotide sequence that is capable of hybridizing with a fragment of the target gene transcript.

RNA may be synthesized either in vivo or in vitro. Endogenous RNA polymerase of the cell may mediate transcription in vivo, or cloned RNA polymerase can be used for transcription in vivo or in vitro. Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus.

Preferably and most conveniently, RNAi can be targeted to an entire polynucleotide sequence of a gene set forth herein. Preferred RNAi molecules of the instant invention are highly homologous or identical to the polynucleotides shown in SEQ ID NO:1. The homology is preferably greater than 90% and is most preferably greater than 95%.

Fragments of genes can also be targeted. These fragments are typically in the approximate size range of about 20 nucleotides. Thus, targeted fragments are preferably at least about 15 nucleotides. In certain embodiments, the gene fragment targeted by the RNAi molecule is about 20–25 nucleotides in length. However, other size ranges can also be used. For example, RNAi "fragments" of about 60 nucleotides with between 95 and 100% identity (to the target gene) can be used.

Genetic regulatory sequences, such as promoters, enhancers, and terminators, can be used in genetic constructs to practice the subject invention. Various constructs can be used to achieve expression in specific plant tissues (by using root specific promoters, for example) and/or to target specific insect pest tissues (by using targeting elements or adjacent targeting sequences, for example).

In a specific embodiment of the subject invention, plant cells are genetically modified to produce at least one RNAi that is designed to be taken up by pests during feeding to block expression (or the function of) of a target gene. As is known in the art, RNAi can target and reduce (and, in some cases, prevent) the translation of a specific gene product. RNAi can be used to reduce or prevent message translation in any tissue of the pest because of its ability to cross tissue and cellular boundaries. Thus, RNAi that is contacted with a pest by soaking, injection, or consumption of a food source will cross tissue and cellular boundaries. RNAi can also be used as an epigenetic factor to prevent the proliferation of subsequent generations of pests.

Polynucleotide sequences disclosed herein can be used to identify conserved nucleotide motifs. Conserved nucleotide motifs strongly suggest that these sequences are functionally conserved. The use of these polynucleotides, and RNAi inhibitors thereof, is advantageous because such RNAi can be designed to have broad RNAi specificity and are thus useful for controlling a large number of pests in planta.

Methods of the subject invention include the transformation of plant cells with genes or polynucleotides of the present invention, which can be used to produce RNAi in the plants. In one embodiment, the transformed plant or plant tissue can express RNAi molecules encoded by the gene or polynucleotide sequence introduced into the plant. Other pesticidal constructs contemplated by the invention include antisense molecules specific to the polynucleotide sequences disclosed herein. The transformation of plants with genetic constructs disclosed herein can be accomplished using techniques well known to those skilled in the art and can involve modification of the gene(s) to optimize expression in the plant to be made resistant to pests. Furthermore, it is known in the art that many tissues of the transgenic plants (such as the leaves, stems, fruit, or roots) can be targeted for transformation.

EXAMPLE 9

The Efficacy of L-Methionine as a *Manduca Sexta* Pesticide in Defined Laboratory Diets or Applied to Host Plant Leaves in an Aqueous Solution The effect of feeding L-methionine to *Manduca sexta* larvae as they progressed from the first through fifth instar stages was determined. Colonies of hornworms are commonly reared for research by well-accepted techniques that account for environmental conditions such as feed availability, daily photoperiod, temperature, etc. The caterpillars were obtained from Carolina Biological Supply Co. and were placed in a lighted 27° C. incubator and fed hydrated reconstituted Dry Tobacco Hornworm Medium Stock No. L-908D (Carolina Biological Supply Co., Burlington, N.C.) supplemented with or without (control) L-methionine supplementation.

The effect of feeding L-methionine to *Manduca sexta* larvae as they progressed from the first through fifth instar stages was studied. In one study, the caterpillars were placed in a 27° C. incubator (photoperiod 16 hours light, 8 hours dark; relative humidity 60%) and fed a hydrated standard defined hornworm diet without (control) or with L-methionine supplementation (10% wt./wt. of dry components). Methionine supplementation prevented all the caterpillars from advancing in development, and killed 100% of the larvae within 3 days. None of the control larvae were killed—indeed all the control larvae were healthy and continued along their developmental course through at least the fifth instar stage (leading to the most crop-destructive stage). The results of this study are shown in FIG. 1.

In another study using defined diet over a 22-day period, the percentage treatment mortality of neonate *Maduca* larvae exposed to different concentrations of methionine was measured. This is shown in Table 3. Sample size was N=60 larvae for each treatment. Significance was determined by one-way ANOVA using a Tukey Multiple Comparison at P=0.001.

TABLE 3

% Mortality on Days After Exposure to Hornworm Defined Diet

| Methionine in diet (% w/w) | Day 0 | Day 2 | Day 4 | Day 6 | Day 8 | Day 10 | Day 12 | Day 14 | Day 16 | Day 18 | Day 20 | Day 22 | $P < 0.001$ Tukey's MCP; $F = 14.27$ |
|---|---|---|---|---|---|---|---|---|---|---|---|---|---|
| | | | | | | Control | | | | | | | |
| 0% | 0.0 | 0.0 | 0.0 | 0.0 | 0.0 | 0.0 | 0.0 | 0.0 | 0.0 | 0.0 | 0.0 | 0.0 | A |
| 0.1% | 0.0 | 0.0 | 4.1 | 35.4 | 35.4 | 35.4 | 35.4 | 35.4 | 35.4 | 35.4 | 35.4 | 35.4 | B |
| 0.3% | 0.0 | 17.0 | 24.5 | 39.6 | 39.6 | 39.6 | 39.6 | 39.6 | 39.6 | 39.6 | 39.6 | 39.6 | BC |
| 0.5% | 0.0 | 18.9 | 22.4 | 35.4 | 35.4 | 35.4 | 35.4 | 35.4 | 50.0 | 50.0 | 50.0 | 62.5 | BC |
| 1% | 0.0 | 24.5 | 38.8 | 50.0 | 82.1 | 82.1 | 82.1 | 82.1 | 82.1 | 82.1 | 82.1 | 100.0 | C |
| 3% | 0.0 | 100.0 | 100.0 | 100.0 | 100.0 | 100.0 | 100.0 | 100.0 | 100.0 | 100.0 | 100.0 | 100.0 | C |
| 5% | 0.0 | 100.0 | 100.0 | 100.0 | 100.0 | 100.0 | 100.0 | 100.0 | 100.0 | 100.0 | 100.0 | 100.0 | C |
| 10% | 0.0 | 100.0 | 100.0 | 100.0 | 100.0 | 100.0 | 100.0 | 100.0 | 100.0 | 100.0 | 100.0 | 100.0 | C |

Figure 2:
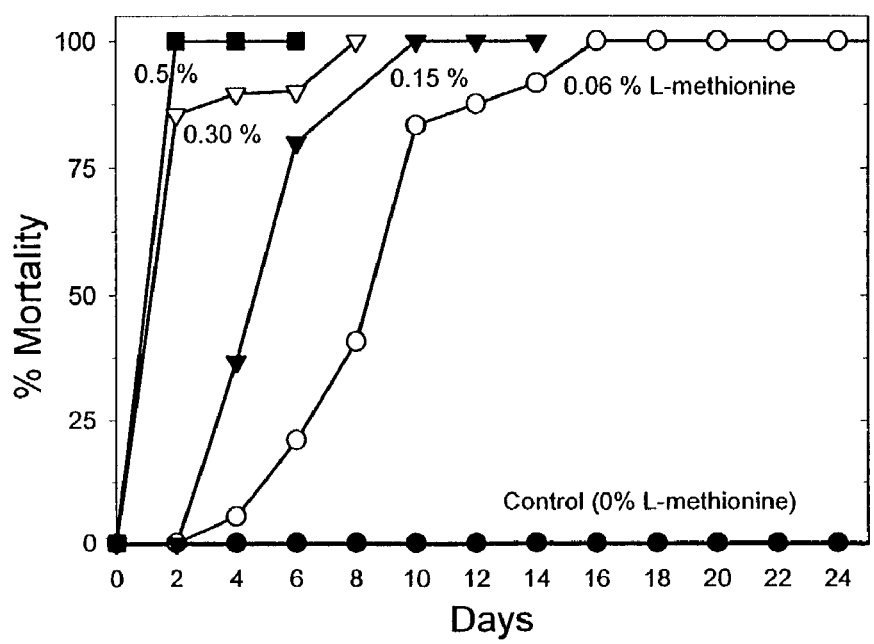
FIG. 2 shows the concentration-dependent efficacy of L-methionine as a *Manduca sexta* pesticide, as applied to eggplant (*Solanum melongena*) host plant leaves using water as vehicle.

Another study evaluated the *Manduca* larvae mortality on excised leaves of host plant (eggplant; *Solanum melongena*) that were sprayed with various concentrations of L-methionine dissolved in deionized water. *Manduca sexta* neonate larvae were initially reared on eggplants in Plexiglas cylinders. Larvae (total N=64/treatment) were exposed to eggplant leaves that were sprayed (then dried) with aqueous solutions of methionine. Larvae of *Manduca sexta* were 100% dead at all test doses, while the control (0% methionine) yielded zero percent mortality. The results of this study are shown in FIG. 2. In a further study, similar results were obtained with using intact plants growing in temperature controlled chambers. In the case of intact host plants, plant viability was not affected by L-methionine treatment, while the control plants were severely damaged by surviving larvae.

EXAMPLE 10

Figure 3:
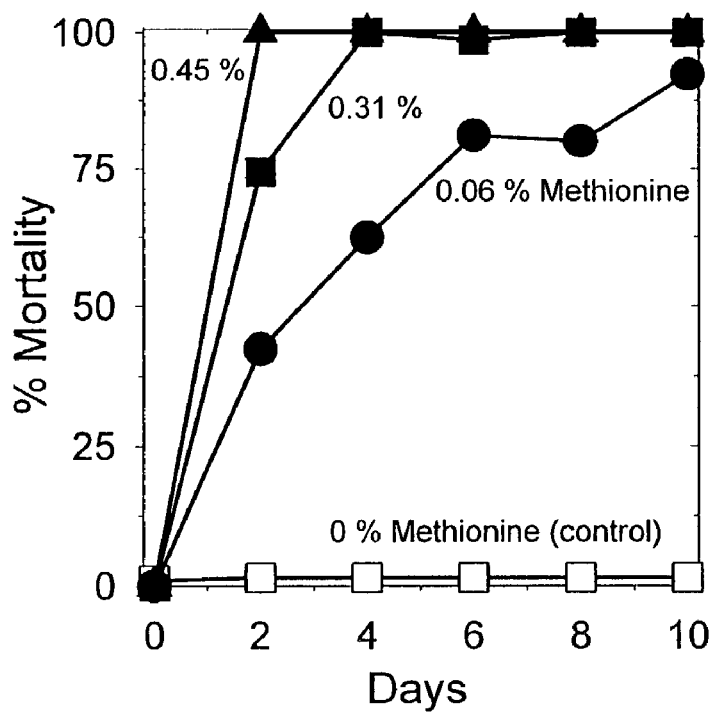
FIG. 3 shows the concentration-dependent efficacy of L-methionine as a *Manduca sexta* pesticide as applied to eggplant (*Solanum melongena*) host plant leaves using a Silwet-L77 solution as vehicle (Silwet L-77 surfactant is a registered trademark of Union Carbide Chemicals & Plastic Technology Corp.).

Efficacy of L-Methionine as a *Manduca sexta* Pesticide on Host Plant Leaves Using a Silwet-L77 Solution In one study, leaves of eggplant (*Solanum melongena*) were sprayed with a deionized water/Silwet-L77 solution containing varying concentrations of methionine, then allowed to dry. The Silwet-L77 was prepared according to the manufacture's instructions. *Manduca sexta* larvae (N=400; 80 per methionine dose) were then exposed to the eggplant leaves during 10 days, and surviving larvae were counted daily. Times to reach complete mortality were: 2 days on leaves treated with 0.45% (w/w) methionine, and 4 days on leaves treated with 0.31% methionine, and 10 to 16 days on leaves treated with 0.06% (w/w) methionine. The results of this study are shown in FIG. 3.

EXAMPLE 11

Figure 4:
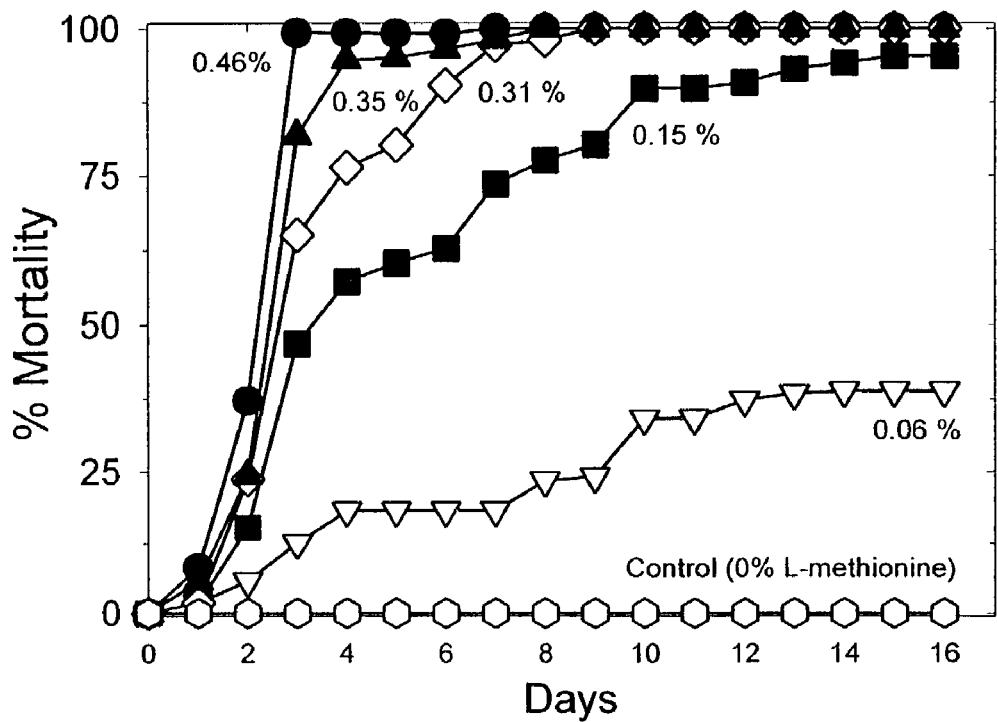
FIG. 4 shows the concentration-dependent efficacy of L-methionine as a Colorado potato beetle (*Leptinotarsa decemlineata*) pesticide, as applied to eggplant (*Solanum melongena*) host plants.

Efficacy of L-Methionine as a *Leptinotarsa decemlineata* Pesticide on Growing Whole Plants Host growing whole eggplants in environmental growth chanmbers were sprayed with deionized water containing varying concentrations of methionine, then dried. *Leptinotarsa decemlineata* larvae (N=160 per group) were exposed to the leaves, and surviving larvae were counted daily. The results of this experiment are shown in FIG. 4. In this example, complete mortality was attained at $\leq 0.15\%$ methionine, compared to zero percent mortality with the control (0% methionine).

EXAMPLE 12

Figure 5:
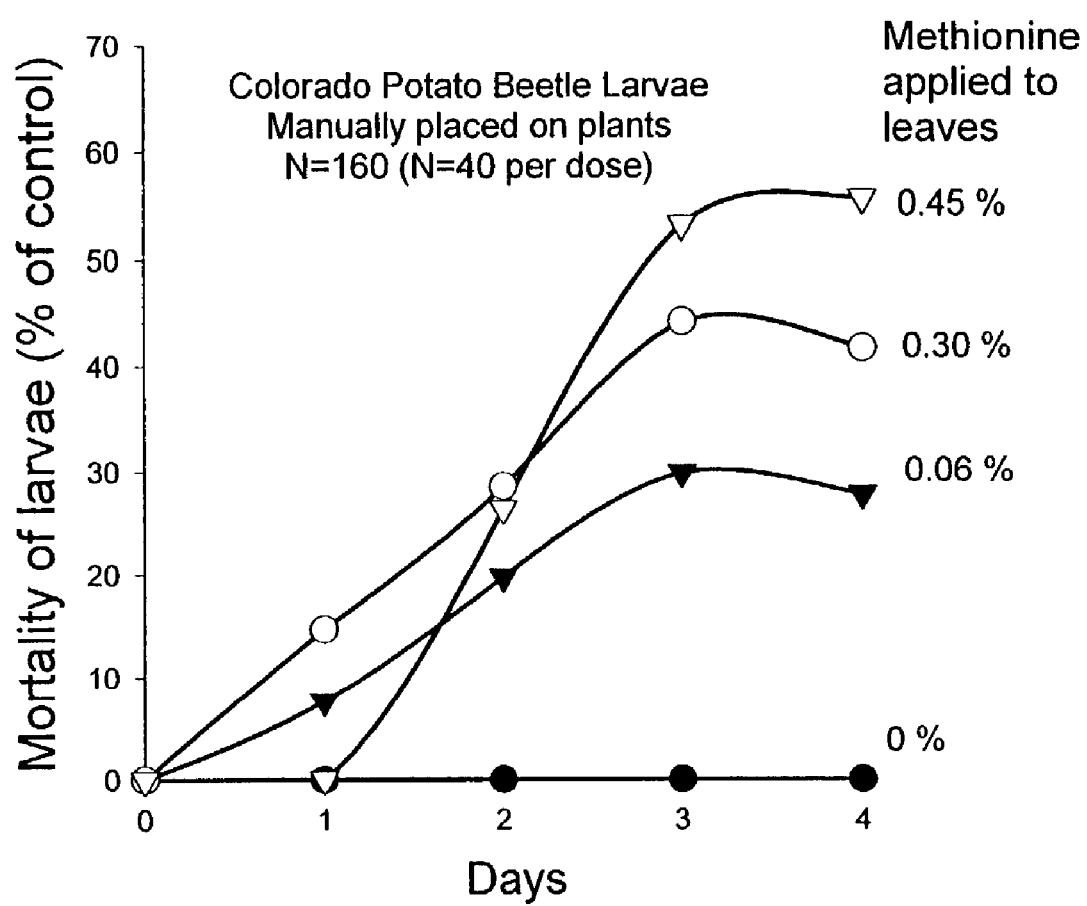
FIG. 5 shows an outside field trial demonstrating concentration-dependent insecticidal efficacy of aqueous L-methionine solutions applied to an eggplant crop (*Solanum melongena*), allowed to dry, then the crop was "seeded" with larvae of Colorado potato beetle, *Leptinotarsa decemlineata*.

Field Trial of the Efficacy of L-Methionine as a *Leptinotarsa decemlineata* Pesticide on Growing Whole Plants Eggplant (*Solanum melongena*) growing in an outside test field were treated with various concentrations of aqueous L-methionine solutions applied to the leaves, which were allowed to dry. Then larvae of Colorado potato beetle, *Leptinotarsa decemlineata*, were applied to the plants, and surviving larvae were counted daily. FIG. 5 shows that the lowest concentration attempted, 0.06% (w/w on leaves), was efficacious, and that larvae mortality increased in a dose-dependent manner.

EXAMPLE 13

Figure 6A:
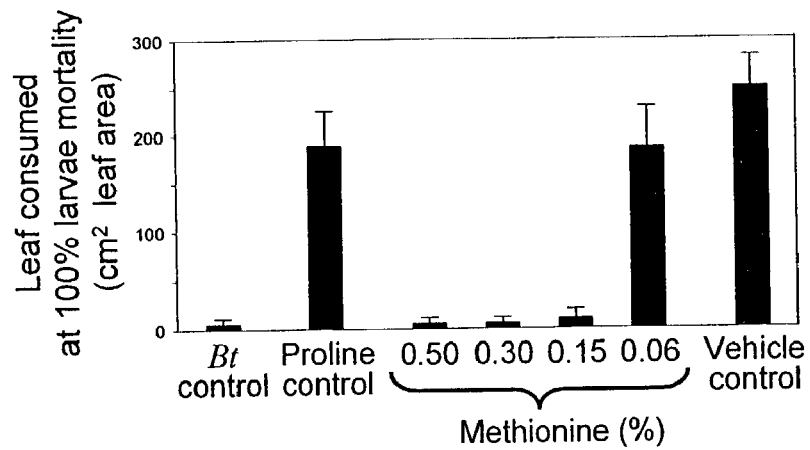
FIG. 6A–C shows that L-methionine insectical treatments do not adversely affect host plant fruit yields or weights of host eggplant (*Solanum melongena*) grown in the field.
Figures 6B, 6C:
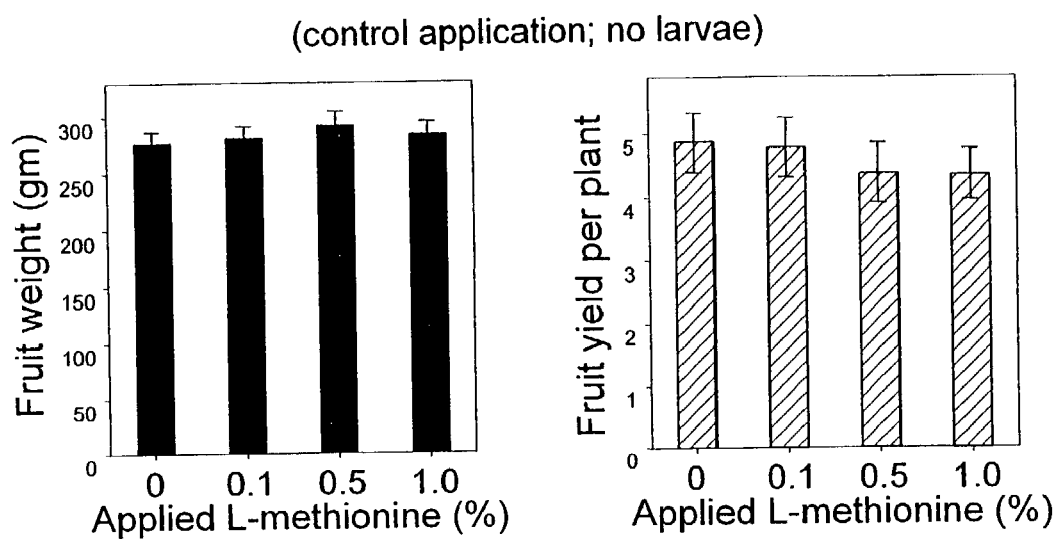

Determination that L-Methionine Treatment for *L. Decemlineata* or *Manduca sexta* does not Adversely Affect Host Plant Fruit Health, Fruit Yields or Fruit Weights Host eggplant (*Solanum melongena*) growing in fields were sprayed with deionized water containing varying concentrations of methionine, then dried. At all L-methionine concentrations, fruit yield mean numbers or mean weights were not significantly different from control (0% methionine) ($P \geq 0.05$ N$\geq$174). The results of this experiment are shown in FIGS. 6A and 6B.

EXAMPLE 14

Assessment of Efficacy of L-Methionine as a Mosquito Pesticide

Figure 7:
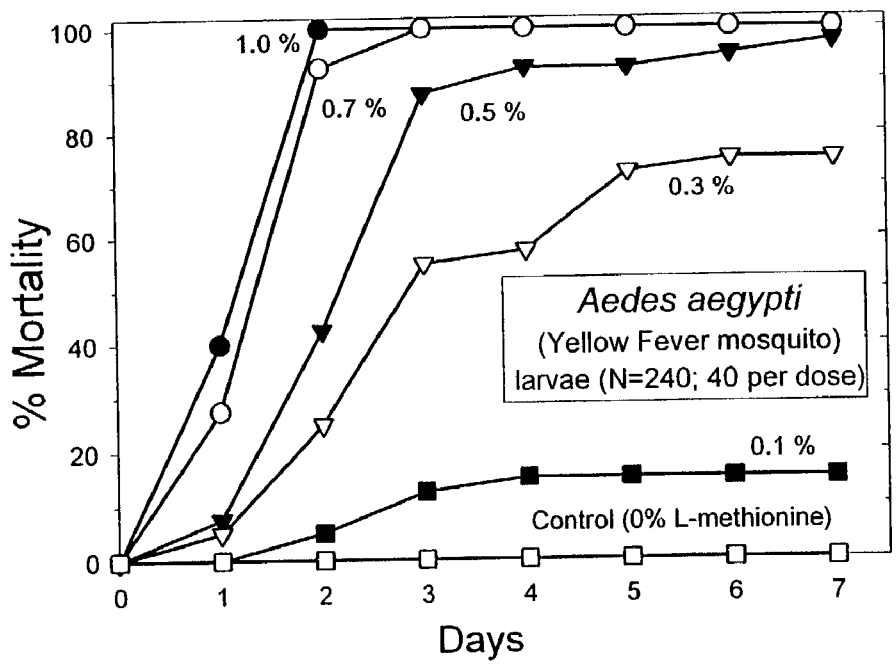
FIG. 7 shows the concentration-dependent efficacy of L-methionine as an *Aedes aegypti* larvae pesticide in pooled standing water.

In this example experiment, *Aedes aegypti* larvae entering the third or fourth instar stages (N=240; 40 per group) were placed in water containing various concentrations of L-methionine. In each solution, larvae fed ad libitum on commercial dried fish food applied to the water. The results of this study are shown in FIG. 7.

EXAMPLE 15

Figure 8:
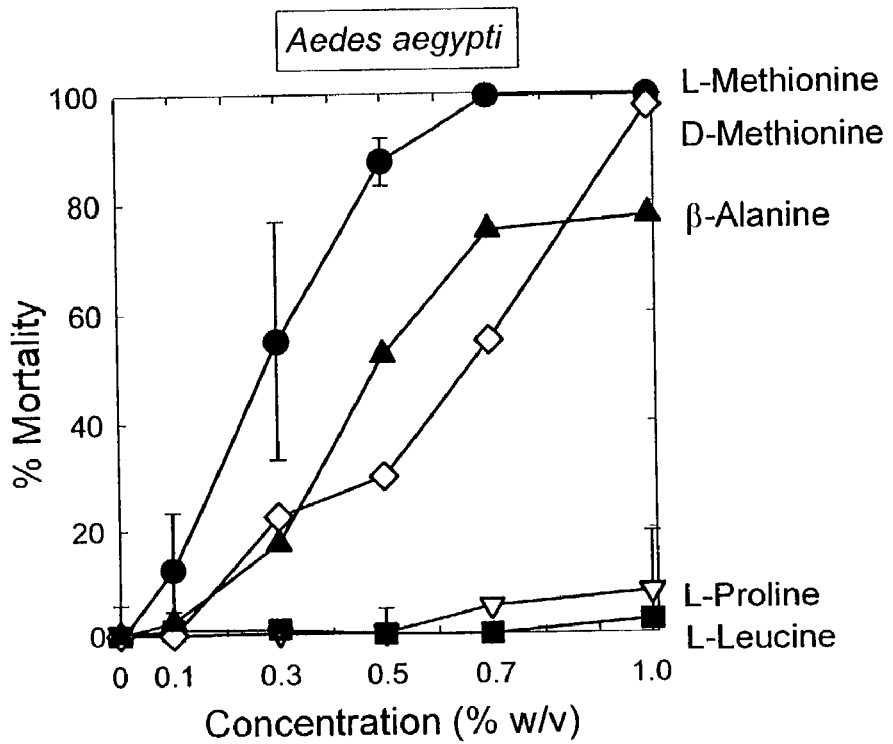
FIG. 8 shows the pesticidal specificity and concentration-dependent efficacy of L-methionine, compared to L-proline, L-lecuine, D-methionine, and β-alanine, on *Aedes aegypti* larvae mortality in pooled standing water.

Assessment of Specificity and Efficacy of L-Methionine as a Mosquito Pesticide Another experiment assessed the specificity of L-methionine compared to L-proline on *Aedes aegypti* survival. Mosquito larvae (third or fourth instar; N=240) were placed in water containing various concentrations of L-proline or L-methionine, and fed ad libitum with commercial dried fish food applied to the water. There was no effect of L-proline compared to 0% methionine control ($P \geq 0.05$) at all test days. However, 0.7% methionine killed 100% larvae with LD50~0.3% methionine on day 3. Similar data were obtained for day 2, which yielded LD50~0.5% methionine. See FIG. 8.

EXAMPLE 16

Pests with Alkaline Gut Compartments

Table 4 provides an illustrative, non-exhaustive, list of pests having alkaline gut compartments (adapted from Nation, J., 2001, In: Insect Physiology and Biochemistry, CRC Press, Boca Raton, pp 496).

TABLE 4

| | The pH in various parts of the gut of selected insects | | | |
|---|---|---|---|---|
| Insect | Foregut | Midgut | Hindgut | Reference |
| | Orthoptera | | | |
| *Phoetaliotes nebrascensis* grasshopper (Acrididae) | 6.03 | 7.12 | 6.11 | (1) |
| *S. gregaria* desert locust | | 5.3 | | (5) |
| *Gryllus rubens* field cricket (Gryllidae) | 5.8–6.0 | 7.4–7.6 | 7.6–7.8 (ant hindgut) | (7) |
| *Gryllus bimaculatus* field cricket (Gryllidae) | 5.84 (crop) | 8.07 (ventriculus) | 8.50 (illeum)  7.59 (rectum) | (20) |
| *Leucophaea madeirae* cockroach (Blattidae) | 9.5 (posterior midgut) | | | (9) |
| | Coleoptera | | | |
| *Popillia japonica* larvae Japanese beetle (Scarabaeidae) | 8.5 | | | (2) |
| *Exomala orientalis* larvae Oriental beetle (Scarabaeidae) | 8.5–9.0 | | | (2) |
| *Rhizotrogus majalis* larvae European chafer (Scarabaeidae) | 9.0–9.5 | | | (2) |
| *Maladera castanea* larvae Asiatic garden beetle (Scarabaeidae) | 8.5 | | | (2) |
| *Lichnanthe vulpina* larvae Cranberry root grub (Scarabaeidae) | 8.5 | | | (2) |
| *Phyllophaga anxia* larvae *Phyllophaga* whitegrub (Scarabaeidae) | 8.5–9.0 | | | (2) |
| *Oryctes nasicornis* (Scarabaeidae) | 12.2 | | | (15) |
| | Lepidoptera | | | |
| *Agrotis ipsilon* black cutworm (Noctuidae) | 8.5–9.0 | | | (2) |
| *Manduca sexta* tobacco hornworm (Sphingidae) | 9.5–9.7 | | | (5) |
| *Manduca sexta* | 6.4 | apical folds of ant. midgut | | (6) |
| | 8.2 | basal folds of ant. midgut | | |
| | 7.2 | Apical folds of post midgut | | |
| | 7.1 | Basal folds of post midgut | | |
| | Diptera | | | |
| mosquito larva | ~10 | | | (14) |
| *Simulium vitatum* Blackfly (Simuliidae) | 11.4 | | | (16) |
| *Tipula abdominalis* cranefly (Tipulidae) | 11.6 | | | (17) |

TABLE 4-continued

| The pH in various parts of the gut of selected insects | | | | |
|---|---|---|---|---|
| Insect | Foregut | Midgut | Hindgut | Reference |
| *Lucilia cuprina* larva blowfly (Calliphoridae) | 7.4–8 anterior midgut | 3.3 middle midgut | 7.4–8 posterior midgut | (18) |
| Isoptera | | | | |
| termites | >10 (ant. midgut) | | | (12) |

References; Many additional references can be found in Berenbaum (1980) and Nation, J., 2001, In: Insect Physiology and Biochemistry, CRC Press, Boca Raton, pp 496).
(1) Barbehenn, R. V., M. M. Martin, and A. E. Hagerman. 1996, Reassessment of the roles of the peritrophic envelope and hydrolysis in protecting polyphagous grasshoppers from ingested hydrolyzable tannins. J. Chem. Ecol. 22: 1911–1929.
(2) Broadway, R. M. and M. G. Villani. 1995. Does host range influence susceptibility of herbivorous insects to non-host plant proteinase inhibitors? Entomol. Exp. et Appl. 76: 303–312.
(3) Murdock, L. L., G. Brookhart, P. E. Dunn, D. E. Foard, S. Kelley, L. Kitch, R. E. Shade, R. H. Shukle, and J. L. Wolfson. 1987. Cysteine digetive proteinases in Coleoptera. Comp. Biochem. Physiol. 87B: 783–787.
(4) Evans, W. A. L., and D. W. Payne. 1964. Carbohydrases of the alimentary tract of the desert locust, *Schistocerca gregaria* Forsk. J. Insect Physiol. 10: 657–674.
(5) Martin, J. S., M. M. Martin, and E. A. Bernays. 1987. Failure of tannic acid to inhibit digestion or reduce digestibility of plant protein in gut fluids of insect herbivores: Implications for theories of plant defense. J. Chem. Ecol. 13: 605–621.
(6) Dow, J. A. T., and M. J. O'Donnell. 1990. Reversible alkalinization by *Manduca sexta* midgut. J. Exp. Biol. 150: 247–256.
(7) Thomas, K. K. and J. L. Nation. 1984. Protease, amylase and lipase activities in the midgut and hindgut of the cricket, *Gryllus rubens* and mole cricket, *Scapteriscus acletus*. Comp.
(8) O'Riordan, A. M. 1969. Electrolyte movement in the isolated midgut of the cockroach (*Periplaneta americana*). J. Exp. Biol. 51: 699–714.
(9) Engelmann, F., and P. M. Geraerts. 1980. The proteases and the protease inhibitor in the midgut of *Leucophaea maderae*. J. Insect Physiol. 26: 703–710.
(10) Martin, M. M., J. J. Kukor, J. S. Martin, D. L. Lawson, and R. W. Merritt. 1981a. Digestive enzymes of larvae of three species of caddisflies (Trichoptera). Insect Biochem. 11: 501–505.
(11) Martin, M. M., J. S. Martin, J. J. Kukor, and R. W. Merritt. 1981b. The digestive enzymes of detritus-feeding stonefly nymphs (Plecoptera; Pteronarcyidae). Can. J. Zool. 59: 1947–1951.
(12) Bignell, D. E., and J. M. Anderson. 1980. Determination of pH and oxygen status in the guts of lower and higher termites. J. Insect Physiol. 26: 183–188.
(13) Mishra, S. C., and P. K. Sen-Sarma. 1981. Hydrogen ion concentration in the digestive tract of three species of Indian termites. Entomon. 6: 131–134.
(14) Dadd, R. H. 1975. Alkalinity within the midgut of mosquito larvae with alkaline-active digestive enzymes. J. Insect Physiol. 21: 1847–1853.
(15) Bayon, C. 1980. Volatile fatty acids and methane production in relation to anaerobic carbohydrate frementation in *Oryctes nasicornis* larvae (Coleoptera: Scarabaeidae). J. Insect Physiol. 26: 819–828.
(16) Undeen (1979)
(17) Martin et al. (1980)
(18) Waterhouse, D. F., and B. Stay. 1955. Functional differentiation in the midgut epithelium of blowfly larvae as revealed by histochemcial tests. Aust. J. Biol. Sci. 8: 253–277.
(19) Krishna, S. S., and K. N. Saxena. 1962. Digestion and absorption of food in *Tribolium castaneum* (Herbst). Physiol. Zool. 35: 66–78.
(20) Teo, L. H. 1997. Tryptic and chymotryptic activites in different parts of the gut of the field cricket *Gryllus bimaculatus*

EXAMPLE 17

Insertion of Toxin Genes into Plants

One aspect of the subject invention is the transformation of plants with genes encoding expression of the pesticidal compounds of the present invention, or genes encoding enzymes or proteins of metabolic pathways leading to pesticidal compounds of the present invention. Such enzymes involve at least, but are not limited to, three major metabolic pathways in plants (see FIG. 9): cystathionine γ-synthase (CGS), cystathionine β-lyase (CBL) and methionine synthase (MS). Furthermore, plants possess several sulfur assimilatory enzymes that contribute to expression of methionine, including but not limited to: ATP-sulfurylase, cysteine synthase and serine acetyltransferase. The transformed plants are resistant to attack by the target insect pest.

Genes encoding pesticidal compounds, as disclosed herein, or genes encoding proteins or enzymes associated with the production of pesticidal compounds, as disclosed herein, can be inserted into plant cells using a variety of techniques that are well known in the art. For example, a large number of cloning vectors comprising a replication system in *E. coli* and a marker that permits selection of the transformed cells are available for transforming higher plants, e,g, pBR322, pUC series, M13mp series, pACYC184, etc. Accordingly, the sequence encoding the pesticidal peptide can be inserted into the vector at a suitable restriction site. The resulting plasmid can be used for transformation into *E. coli*. The *E. coli* cells can be cultivated in a suitable nutrient medium, then harvested and lysed. The plasmid can be recovered. Sequence analysis, restriction analysis, electrophoresis, and other biochemical and/or molecular biological methods can be generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti plasmid (the tumor-inducing plasmid of the plant-pathogenic bacterium *Agrobacterium tumefaciens*) or Ri plasmid (the root-inducing plasmid of *Agrobacterium rhizogenes*) can be used for the transformation of the plant cell, then at least the right border, but often the right and the left border of the Ti or Ri plasmid T-DNA ("Transferred DNA"), must be joined as the flanking region of the genes to be inserted.

A large number of techniques are available for inserting DNA into a plant host cell. These techniques include transformation with T-DNA using *Agrobacterium tumefaciens* or *Agrobacterium rhizogenes* as transformation agent, fusion, injection, biolistics (microparticle bombardment), or electroporation as well as other possible methods.

One of the most widely used approaches for the introduction of DNA into plant cells exploits the natural DNA-transferring properties of *Agrobacterium tumefaciens* and *Agrobacterium rhizogenes*, the two species which cause crown gall and hairy root. Their ability to cause disease depends on the presence of large plasmids, in excess of 100 kb, which are referred to as the Ti and Ri plasmids, respectively.

A region referred to as the T-DNA ("Transferred DNA") is transferred from an infecting *Agrbacterium* cell into the nucleus of the plant cell, where it is integrated into the plant genome. The use of T-DNA for the transformation of plant cells has been intensively researched and sufficiently described in Eur. Pat. Appl. No. EP 120 516; Hoekema (In: The Binary Plant Vector syste, Offset-durkkerij, Kanters, B. V., Alblasserdam, Chapter 5, 1985); An et al. (1985, *EMBO J.* 4:277–287); Herrera-Estrella et al. (1983, *Nature* 303: 209); Bevan et al. (1983, *Nature* 304:184), and Klee et al (1985, *Bio/Technology* 3:637–642). Transfer of the T-DNA depends on a set of genes called vir if they are on the Ti plasmid, or chv if they are on the chromosome. These genes: are induced in response to various compounds in exudates from wounded plants. The T-DNA itself is flanked by repeated sequences of around 25 base pairs, called border repeats (or left and right borders). The T-DNA contains a group of genes referred to as the one genes, which are responsible for the oncogenicity of the T-DNA.

The use of *Agrobacterium* in the genetic manipulation of plants involves the insertion of foreign DNA into the T-DNA of a bacterial cell and subsequent transfer of the DNA by the transformed bacterium into the plant. As long as the necessary proteins are provided by the bacterium, any sequences flanked by the T-DNA border repeats can be transferred into the recipient plant cell genome. The Ti plasmids are too large to manipulate directly, but this problem can be circumvented by using cointegrative and binary systems.

The two main components of a cointegrative system are a Ti plasmid that has typically been modified by the replacement of material between the border repeats (including the one sequences) by pBR322; and an intermediate vector, which is a modified pBR322 containing an extra marker, such as kanamycin resistance. The gene to be introduced into the target plant is first cloned into the intermediate vector, and this construct is then introduced into *Agrbacterium* containing the Ti vector. The pBR322-based plasmid cannot replicate efficiently inside *Agrbacterium*, so selection for kanamycin resistance identifies those *Agrbacterium* cells where the pBR322-based intermediate plasmid has been integrated by homologous recombination into the Ti plasmid. Because the recombination is homologous, it will take place across the pBR322 sequences and therefore result in integration between the border repeats.

The need for counteraction of the plasmids can be circumvented by use of a binary vector, such as pBin19, a small plasmid containing a pair of left and right borders. The lacZ region, located within the borders, facilitates insertion and detection of DNA. A neomycin phosphotransferase gene, typically modified for expression in plants by addition of nopaline synthase expression sequences, is also present within the borders. Outside the left and right borders, there is typically a kanamycin resistance gene that will function in prokaryotes and a broad host-range origin derived from the plasmid pRK252. The proteins that catalyze transfer of the T-DNA into the host plant do not have to be cis-encoded (i.e., do not have to be encoded by the same molecule). Therefore, if the binary vector is introduced into *Agrbacterium* that already contains a resident Ti plasmid, the resident plasmid can provide all the functions needed to transfer into a plant nucleus the DNA between the borders of the binary vector. Other, more sophisticated binary vectors, are also known in the art, for example pROK1. These vectors typically have plant promoters incorporated to drive expression. Others have cos sites to allow packaging into lambda phage heads.

When the correct sequences have been incorporated into a vector (whether binary or cointegrative), the vector must then be transferred to an *Agrbacterium* strain carrying an appropriate Ti plasmid. This is usually accomplished either by electroporation with naked DNA or by a triparental mating involving the *Agrbacterium* strain, an *E. coli* strain containing the vector to be transferred, and an *E. coli* strain with a plasmid capable of mobilizing the binary or intermediate vector into *Agrbacterium*.

Once the binary vector of the cointegrative vector has been introduced into a suitable *Agrbacterium* strain (and counteraction has occurred), the next stage is to permit the *Agrbacterium* to infect plant cells. Various methods exist, including inoculation of intact plants with *Agrbacterium* cultures by injection, but the most widely used is to incubate discs cut from leaves of the target plant with an *Agrbacterium* culture. The bacterium will attack cells around the edge of the wounded leaf disc and transfer its T-DNA back into them. The leaf discs are then transferred to a suitable medium to select for transformation. The neomycin phosphotransferase gene is widely used, conferring resistance to aminoglycoside antibiotics, such as neomycin, kanamycin, and G518. On a suitable selective medium, shoots form around the edges of the treated leaf discs. The shoots can then be regenerated into intact plants. See Howe, *Gene Cloning and Manipulation* 1995, Cambridge University Press, New York.

The transformed cells are regenerated into morphologically normal plants in the usual manner. If a transformation event involves a germ line cell, then the inserted DNA and corresponding phenotypic trait(s) will be transmitted to progeny plants. Such plants can be grown in the normal manner and crossed with plants that have the same transformed hereditary factors or other hereditary factors. The resulting hybrid individuals have the corresponding phenotypic properties.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application

We claim:

1. A method for killing a pest having an alkaline gut compartment, wherein said pest is an insect or nematode, wherein said method comprises feeding said pest a compound which disrupts, within said pest, an organic solute transporter/ligand-gated ion channel protein to cause death of the pest, and wherein said compound is D-methionine, DL-methionine, or hydroxy-methionine.

2. The method, according to claim 1, wherein said pest is selected from the group consisting of Lepidopterans, Coleopterans, Diptera, and Blaiiaria, and Isoptera.

3. The method, according to claim 2, wherein said pest is in the order Coloptera.

4. The method, according to claim 3, wherein said coleopteran is a *Leptinotarsa* spp., rootworm, or weevil.

5. The method, according to claim 2, wherein said lepidopteran is selected from the group consisting of cutworms, budworms, leafworms, carworms, and armyworms.

6. The method, according to claim 2, wherein said pest is in the order Diptera.

7. The method, according to claim 6, wherein said dipteran is a mosquito.

8. The method, according to claim 1, wherein said pest is selected from the group consisting of cockroaches, ants, termites, and nematodes.

9. The method, according to claim 1, wherein said pest has a V-type ATPase.

10. A method for killing a pest having an alkaline gut compartment, wherein said pest is an insect or nematode, wherein said method comprises administering to said pest an effective amount of D-methionine, DL-methionine, or hydroxy-methionine to cause death of the pest.

11. A method for killing a pest having an alkaline gut compartment, wherein said pest is an insect or nematode, wherein said method comprises inhibiting, within said pest, solute transport or ion channel activity to cause death of the pest, and wherein said inhibition is caused by feeding said pest D-methionine, DL-methionine, or the hydroxy-methionine.

* * * * *

UNITED STATES PATENT AND TRADEMARK OFFICE
CERTIFICATE OF CORRECTION

PATENT NO. : 7,181,884 B2
APPLICATION NO. : 10/298974
DATED : February 27, 2007
INVENTOR(S) : Bruce R. Stevens, James P. Cuda and Lewis S. Long It is certified that error appears in the above-identified patent and that said Letters Patent is hereby corrected as shown below:

Column 34,
Line 29, "*Manduca Sexta*" should read --*Manduca sexta*--.

Column 41,
Lines 27-28, "These genes: are induced" should read --These genes are induced--.

Column 41,
Line 32, "one genes" should read --*onc* genes--.

Column 41,
Line 48, "one sequences" should read --*onc* sequences--.

Column 41,
Lines 52-53, "*Agrbacterium*" should read --*Agrobacterium*--.

Column 42,
Lines 10-11, "*Agrbacterium*" should read --*Agrobacterium*--.

Column 42,
Line 22, "*Agrbacterium*" should read --*Agrobacterium*--.

Column 42,
Line 25, "*Agrbacterium*" should read --*Agrobacterium*--.

Column 42,
Line 28, "*Agrbacterium*" should read --*Agrobacterium*--.

Column 42,
Line 30, "*Agrbacterium*" should read --*Agrobacterium*--.

Column 42,
Line 32, "*Agrbacterium*" should read --*Agrobacterium*--.

Column 42,
Line 33, "*Agrbacterium*" should read --*Agrobacterium*--.

Column 42,
Line 35, "*Agrbacterium*" should read --*Agrobacterium*--.

Column 57,
Line 67, "Diptera, and Blaiiaria" should read --Diptera, Blattaria--.

UNITED STATES PATENT AND TRADEMARK OFFICE
CERTIFICATE OF CORRECTION

| | | |
|---|---|---|
| PATENT NO. | : 7,181,884 B2 | |
| APPLICATION NO. | : 10/298974 | |
| DATED | : February 27, 2007 | |
| INVENTOR(S) | : Bruce R. Stevens, James P. Cuda and Lewis S. Long | |

It is certified that error appears in the above-identified patent and that said Letters Patent is hereby corrected as shown below:

<u>Column 58,</u>
Line 57, "Coloptera" should read --Coleoptera--.

<u>Column 58,</u>
Line 63, "leafworms, carworms" should read --leafworms, earworms--.

Signed and Sealed this

Seventeenth Day of July, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,181,884 B2 | Page 1 of 1 |
| APPLICATION NO. | : 10/298974 | |
| DATED | : February 27, 2007 | |
| INVENTOR(S) | : Bruce R. Stevens et al. | |

It is certified that error appears in the above-identified patent and that said Letters Patent is hereby corrected as shown below:

In the Specification

Column 1:

Lines 13-16, "The subject invention was made with funding from the National Institutes of Health (Grant No. AI 030464). Accordingly, the government may have certain rights in this invention." should read -- The subject invention was made with funding from the National Institutes of Health (Grant No. AI 030464). The government has rights in this invention. --

Signed and Sealed this
Nineteenth Day of August, 2014

Michelle K. Lee
*Deputy Director of the United States Patent and Trademark Office*

SEQUENCE LISTING

<160> NUMBER OF SEQ ID NOS: 27

<210> SEQ ID NO 1
<211> LENGTH: 2860
<212> TYPE: DNA
<213> ORGANISM: Manduca sexta

<400> SEQUENCE: 1

| | | | | | |
|---|---|---|---|---|---|
| ggcacgaggt | tacttgttgg | aggaactgtt | tggcggtggt | gcgatcgatt tctgaacaca | 60 |
| atacacctaa | acacattgca | agtgtgatat | tgtggacaaa | atgaatgacg gccaagtaaa | 120 |
| cggcggtttc | gagtcgtcgg | agcccaagat | ggaaccaaaa | cgatcatcgc aaataagttt | 180 |
| acctccagca | aataataaag | cggctctgga | taatatagat | gacacggact tagaggctga | 240 |
| accgccagaa | cgtatggtat | ggtccaacaa | cattgaattc | ttgatgtcct gcatcgctac | 300 |
| atccgtcggt | ttgggtaacg | tgtggcggtt | ccctttcatc | gcgtaccaga atggaggagg | 360 |
| tgctttcctg | gtgccatacg | tcatcgttct | tttacttgtc | ggcaagcctg tgtactactt | 420 |
| agagtgtgtc | ctcggacaat | tcagttcaag | aaactctgtt | aaagtttggt caatttcacc | 480 |
| ggccatgaaa | ggtactggat | acgctcaagc | tgccggctgc | ggttacatcc tgtcttacta | 540 |
| cgtggtgatc | tgtggtctct | gtctgtatta | cttagctatg | agcttccagg ccactcttcc | 600 |
| atgggctatt | tgtcagcctg | agtgggagaa | ctgcgtaccc | tcagatccaa cacttgctgc | 660 |
| atcagtcaac | aacatcacca | atggtaccag | cagtgctcaa | ctctactttt tgagaacagt | 720 |
| tctccaacaa | agcgatggaa | ttgaaggagg | tctcggtgcc | cccatctggt acttggtgtt | 780 |
| gtgtctattc | atcgcatggc | tcatggtgtt | cggagtcgtc | gcccgaggag tcaagagttc | 840 |
| cggcaaagcg | gcctacttcc | tcgcgctctt | cccatacgtt | gtcatgatca ctttattcat | 900 |
| caccacaatc | atcctgcccg | gtgctactga | cggcatcctg | ttcttcgtca cgcctcaatg | 960 |
| ggcgaaactc | cttgagctcg | gtgtatggta | ctcagcagtc | acgcaagtgt tcttctctct | 1020 |
| gacagtgtgc | accggaccga | tcatcatgtt | ctcctcttac | aacggtttca gacataatat | 1080 |
| ctacagggat | gcttggattg | ttacgacttt | ggacaccttt | acaagtttct tgtctgggtg | 1140 |
| cacgatcttc | ggtatccttg | gtaacctcgc | gtacgaactc | aactcagagg tgggagatgt | 1200 |
| ggtcggtgct | ggcggtacca | gtcttgcttt | catttcatac | cctgatgcca ttgccaaaac | 1260 |
| attccaacct | cagctattct | cggtgctgtt | cttcctgatg | atgtcggtgc tgggtatcgg | 1320 |
| ctcatccgtg | gctctgctat | cgactttcaa | cacattggcg | atggacgcgt tcccacgtgt | 1380 |
| acccaccgtc | tacatgtcag | cgatgacctg | ttcttgcggt | ttcctgcttg acttgtttta | 1440 |
| ctgcacaccg | ggtggacaat | atattcttga | gcttgtagat | cactacggtg gaacattcct | 1500 |
| tgtgcttttc | tgcgccattt | ctgaactcgc | aggcgtgttc | tggatttatg gattggagaa | 1560 |
| tctgtgccta | gacattgagt | tcatgttggg | taaaaagact | ggtgcttact ggcgtctctg | 1620 |
| ctggggcgta | atcactcctg | ctataatgac | gactgtgttc | ttctacgctc ttctcgcctc | 1680 |
| taacaacctg | tgttcggag | acaactacgt | atacccgact | gctggttatg tttctggata | 1740 |
| cttgatgtta | tttttgggca | tgacgtttgt | gccaattgga | attggatttt ctttgtacaa | 1800 |
| ataccgtacc | ggaaccttca | gcgagacgat | caagaaagcc | ttccactcca aaccctcatg | 1860 |
| gggtccccgc | tcgccgagag | agcgtagaga | atggatgcag | ttcaaggctg aagcgaaagc | 1920 |
| tcttagacaa | aagatgaaca | catcacgcgt | caagcactta | tggtacagta tcacgggtgc | 1980 |
| ttacaggcgt | aatattaatt | agctaataaa | atattatgta | aaatatgtac aaatctatac | 2040 |

-continued

```
ctactgatca cttagtggaa attaataggc tagttctaac ttcccttctt aactttatga   2100
caaaggtcat aatgtaacgc gtttatcaaa tggcgaggaa aggcgaatca tacaagaatc   2160
tatgacgcat gctaaaatac attttcattg tattggtact tctggctctt agttgtataa   2220
gtatatgttt atgttaaatt atattcggtg ccatatcata taatacctgc tgtaacgtta   2280
aataacattt tttacactgg taacactctt tctgcaataa ggaaagactg atagtaaatg   2340
aagatttatt gactagtaat aatagactaa attttcataa taaaatcatg taaaaacaaa   2400
ccatttatca cgtagacgca agatcagaga taagtacatg ttaaagaata ttatgtaaaa   2460
ccaattgcta aaaatcaaac ttcataaata ctcatagctt atgaaggaat tgttgttatc   2520
tatacatata ccggtgtcga tattatacat gttacgattt tatttaactt attaccatac   2580
gtgtcgttaa atagatttat atacttatgt tgcaaagtcg atgctatatc gttaggacct   2640
atatggtctt gcgtttgatt ttatagctat tcgatagagt actactacac tattcaaata   2700
gtacgtaata aataaaaagt cttgaaaaat cttcaagaac tctgtgcaac atatttataa   2760
ctttattatt tacagtttca tataagtttc aaggtattgt aatttattat ttaattaatc   2820
gataataaaa tatatcccaa ataaaaaaaa aaaaaaaaa                          2860
```

<210> SEQ ID NO 2
<211> LENGTH: 633
<212> TYPE: PRT
<213> ORGANISM: Manduca sexta

<400> SEQUENCE: 2

| | | | | | | | | | | | | | | |
|---|---|---|---|---|---|---|---|---|---|---|---|---|---|---|
| Met | Asn | Asp | Gly | Gln | Val | Asn | Gly | Gly | Phe | Glu | Ser | Ser | Glu | Pro | Lys |
| 1 | | | | 5 | | | | | 10 | | | | | 15 | |
| Met | Glu | Pro | Lys | Arg | Ser | Ser | Gln | Ile | Ser | Leu | Pro | Pro | Ala | Asn | Asn |
| | | | 20 | | | | | 25 | | | | | 30 | | |
| Lys | Ala | Ala | Leu | Asp | Asn | Ile | Asp | Asp | Thr | Asp | Leu | Glu | Ala | Glu | Pro |
| | | 35 | | | | | 40 | | | | | 45 | | | |
| Pro | Glu | Arg | Met | Val | Trp | Ser | Asn | Asn | Ile | Glu | Phe | Leu | Met | Ser | Cys |
| 50 | | | | | 55 | | | | | 60 | | | | | |
| Ile | Ala | Thr | Ser | Val | Gly | Leu | Gly | Asn | Val | Trp | Arg | Phe | Pro | Phe | Ile |
| 65 | | | | | 70 | | | | | 75 | | | | | 80 |
| Ala | Tyr | Gln | Asn | Gly | Gly | Gly | Ala | Phe | Leu | Val | Pro | Tyr | Val | Ile | Val |
| | | | | 85 | | | | | 90 | | | | | 95 | |
| Leu | Leu | Leu | Val | Gly | Lys | Pro | Val | Tyr | Tyr | Leu | Glu | Cys | Val | Leu | Gly |
| | | | 100 | | | | | 105 | | | | | 110 | | |
| Gln | Phe | Ser | Ser | Arg | Asn | Ser | Val | Lys | Val | Trp | Ser | Ile | Ser | Pro | Ala |
| | | 115 | | | | | 120 | | | | | 125 | | | |
| Met | Lys | Gly | Thr | Gly | Tyr | Ala | Gln | Ala | Ala | Gly | Cys | Gly | Tyr | Ile | Leu |
| 130 | | | | | 135 | | | | | 140 | | | | | |
| Ser | Tyr | Tyr | Val | Val | Ile | Cys | Gly | Leu | Cys | Leu | Tyr | Tyr | Leu | Ala | Met |
| 145 | | | | | 150 | | | | | 155 | | | | | 160 |
| Ser | Phe | Gln | Ala | Thr | Leu | Pro | Trp | Ala | Ile | Cys | Gln | Pro | Glu | Trp | Glu |
| | | | | 165 | | | | | 170 | | | | | 175 | |
| Asn | Cys | Val | Pro | Ser | Asp | Pro | Thr | Leu | Ala | Ala | Ser | Val | Asn | Asn | Ile |
| | | | 180 | | | | | 185 | | | | | 190 | | |
| Thr | Asn | Gly | Thr | Ser | Ser | Ala | Gln | Leu | Tyr | Phe | Leu | Arg | Thr | Val | Leu |
| | | 195 | | | | | 200 | | | | | 205 | | | |
| Gln | Gln | Ser | Asp | Gly | Ile | Glu | Gly | Gly | Leu | Gly | Ala | Pro | Ile | Trp | Tyr |
| | 210 | | | | | 215 | | | | | 220 | | | | |

```
Leu Val Leu Cys Leu Phe Ile Ala Trp Leu Met Val Phe Gly Val Val
225                 230                 235                 240

Ala Arg Gly Val Lys Ser Ser Gly Lys Ala Ala Tyr Phe Leu Ala Leu
                245                 250                 255

Phe Pro Tyr Val Val Met Ile Thr Leu Phe Ile Thr Thr Ile Ile Leu
            260                 265                 270

Pro Gly Ala Thr Asp Gly Ile Leu Phe Phe Val Thr Pro Gln Trp Ala
        275                 280                 285

Lys Leu Leu Glu Leu Gly Val Trp Tyr Ser Ala Val Thr Gln Val Phe
290                 295                 300

Phe Ser Leu Thr Val Cys Thr Gly Pro Ile Ile Met Phe Ser Ser Tyr
305                 310                 315                 320

Asn Gly Phe Arg His Asn Ile Tyr Arg Asp Ala Trp Ile Val Thr Thr
                325                 330                 335

Leu Asp Thr Phe Thr Ser Phe Leu Ser Gly Cys Thr Ile Phe Gly Ile
            340                 345                 350

Leu Gly Asn Leu Ala Tyr Glu Leu Asn Ser Glu Val Gly Asp Val Val
        355                 360                 365

Gly Ala Gly Gly Thr Ser Leu Ala Phe Ile Ser Tyr Pro Asp Ala Ile
370                 375                 380

Ala Lys Thr Phe Gln Pro Gln Leu Phe Ser Val Leu Phe Phe Leu Met
385                 390                 395                 400

Met Ser Val Leu Gly Ile Gly Ser Ser Val Ala Leu Leu Ser Thr Phe
                405                 410                 415

Asn Thr Leu Ala Met Asp Ala Phe Pro Arg Val Pro Thr Val Tyr Met
            420                 425                 430

Ser Ala Met Thr Cys Ser Cys Gly Phe Leu Leu Gly Leu Val Tyr Cys
        435                 440                 445

Thr Pro Gly Gly Gln Tyr Ile Leu Glu Leu Val Asp His Tyr Gly Gly
450                 455                 460

Thr Phe Leu Val Leu Phe Cys Ala Ile Ser Glu Leu Ala Gly Val Phe
465                 470                 475                 480

Trp Ile Tyr Gly Leu Glu Asn Leu Cys Leu Asp Ile Glu Phe Met Leu
                485                 490                 495

Gly Lys Lys Thr Gly Ala Tyr Trp Arg Leu Cys Trp Gly Val Ile Thr
            500                 505                 510

Pro Ala Ile Met Thr Thr Val Phe Phe Tyr Ala Leu Leu Ala Ser Asn
        515                 520                 525

Asn Leu Val Phe Gly Asp Asn Tyr Val Tyr Pro Thr Ala Gly Tyr Val
530                 535                 540

Ser Gly Tyr Leu Met Leu Phe Leu Gly Met Thr Phe Val Pro Ile Gly
545                 550                 555                 560

Ile Gly Phe Ser Leu Tyr Lys Tyr Arg Thr Gly Thr Phe Ser Glu Thr
                565                 570                 575

Ile Lys Lys Ala Phe His Ser Lys Pro Ser Trp Gly Pro Arg Ser Pro
            580                 585                 590

Arg Glu Arg Arg Glu Trp Met Gln Phe Lys Ala Glu Ala Lys Ala Leu
        595                 600                 605

Arg Gln Lys Met Asn Thr Ser Arg Val Lys His Leu Trp Tyr Ser Ile
610                 615                 620

Thr Gly Ala Tyr Arg Arg Asn Ile Asn
625                 630
```

```
<210> SEQ ID NO 3
<211> LENGTH: 20
<212> TYPE: DNA
<213> ORGANISM: Artificial Sequence
<220> FEATURE:
<223> OTHER INFORMATION: Sense Primer "S34"
<220> FEATURE:
<221> NAME/KEY: misc_feature
<222> LOCATION: (3)..(3)
<223> OTHER INFORMATION: Inosine
<220> FEATURE:
<221> NAME/KEY: misc_feature
<222> LOCATION: (6)..(6)
<223> OTHER INFORMATION: Could be c or t
<220> FEATURE:
<221> NAME/KEY: misc_feature
<222> LOCATION: (9)..(9)
<223> OTHER INFORMATION: Inosine
<220> FEATURE:
<221> NAME/KEY: misc_feature
<222> LOCATION: (13)..(13)
<223> OTHER INFORMATION: Could be a or c
<220> FEATURE:
<221> NAME/KEY: misc_feature
<222> LOCATION: (15)..(15)
<223> OTHER INFORMATION: Could be a, g, c, or t
<220> FEATURE:
<221> NAME/KEY: misc_feature
<222> LOCATION: (18)..(18)
<223> OTHER INFORMATION: Could be c or t

<400> SEQUENCE: 3
ggnaangtnt ggngnttncc                                           20

<210> SEQ ID NO 4
<211> LENGTH: 7
<212> TYPE: PRT
<213> ORGANISM: Artificial Sequence
<220> FEATURE:
<223> OTHER INFORMATION: Peptide motif

<400> SEQUENCE: 4

Gly Asn Val Trp Arg Phe Pro
1               5

<210> SEQ ID NO 5
<211> LENGTH: 18
<212> TYPE: DNA
<213> ORGANISM: Artificial sequence
<220> FEATURE:
<223> OTHER INFORMATION: Antisense primer "S21"
<220> FEATURE:
<221> NAME/KEY: misc_feature
<222> LOCATION: (1)..(1)
<223> OTHER INFORMATION: Inosine
<220> FEATURE:
<221> NAME/KEY: misc_feature
<222> LOCATION: (4)..(4)
<223> OTHER INFORMATION: Could be a, g, or t
<220> FEATURE:
<221> NAME/KEY: misc_feature
<222> LOCATION: (7)..(7)
<223> OTHER INFORMATION: Inosine
<220> FEATURE:
<221> NAME/KEY: misc_feature
<222> LOCATION: (10)..(10)
<223> OTHER INFORMATION: Inosine
<220> FEATURE:
<221> NAME/KEY: misc_feature
<222> LOCATION: (13)..(13)
<223> OTHER INFORMATION: Could be a, g, c, or t
<220> FEATURE:
<221> NAME/KEY: misc_feature
<222> LOCATION: (16)..(16)
<223> OTHER INFORMATION: Could be a or g
```

```
<400> SEQUENCE: 5
ngcnatngcn tcnggnta                                              18

<210> SEQ ID NO 6
<211> LENGTH: 6
<212> TYPE: PRT
<213> ORGANISM: Artificial Sequence
<220> FEATURE:
<223> OTHER INFORMATION: Peptide motif
<220> FEATURE:
<221> NAME/KEY: MISC_FEATURE
<222> LOCATION: (3)..(3)
<223> OTHER INFORMATION: Could be Asp or Glu

<400> SEQUENCE: 6

Tyr Pro Xaa Ala Ile Ala
1               5

<210> SEQ ID NO 7
<211> LENGTH: 20
<212> TYPE: DNA
<213> ORGANISM: Artificial Sequence
<220> FEATURE:
<223> OTHER INFORMATION: Sense primer "S22"
<220> FEATURE:
<221> NAME/KEY: misc_feature
<222> LOCATION: (3)..(3)
<223> OTHER INFORMATION: Inosine
<220> FEATURE:
<221> NAME/KEY: misc_feature
<222> LOCATION: (6)..(6)
<223> OTHER INFORMATION: Could be c or t
<220> FEATURE:
<221> NAME/KEY: misc_feature
<222> LOCATION: (9)..(9)
<223> OTHER INFORMATION: Inosine
<220> FEATURE:
<221> NAME/KEY: misc_feature
<222> LOCATION: (13)..(13)
<223> OTHER INFORMATION: Could be g or t
<220> FEATURE:
<221> NAME/KEY: misc_feature
<222> LOCATION: (15)..(15)
<223> OTHER INFORMATION: Could be a, g, c or t
<220> FEATURE:
<221> NAME/KEY: misc_feature
<222> LOCATION: (18)..(18)
<223> OTHER INFORMATION: Could be c or t

<400> SEQUENCE: 7
ggnaangtnt ggngnttncc                                            20

<210> SEQ ID NO 8
<211> LENGTH: 22
<212> TYPE: DNA
<213> ORGANISM: Artificial Sequence
<220> FEATURE:
<223> OTHER INFORMATION: Sense primer "S25" (S25TrueFOR)

<400> SEQUENCE: 8
aacacttgct gcatcagtca ac                                         22

<210> SEQ ID NO 9
<211> LENGTH: 21
<212> TYPE: DNA
<213> ORGANISM: Artificial Sequence
<220> FEATURE:
<223> OTHER INFORMATION: Antisense primer "S26"
```

```
<400> SEQUENCE: 9
ctcaaggagt ttcgcccatt g                                              21

<210> SEQ ID NO 10
<211> LENGTH: 36
<212> TYPE: DNA
<213> ORGANISM: Artificial Sequence
<220> FEATURE:
<223> OTHER INFORMATION: Primer "AP" (Gibco Life Technologies)

<400> SEQUENCE: 10
ggccacgcgt cgactagtac tttttttttt tttttt                              36

<210> SEQ ID NO 11
<211> LENGTH: 49
<212> TYPE: DNA
<213> ORGANISM: Artificial Sequence
<220> FEATURE:
<223> OTHER INFORMATION: Primer "PA142_AP"

<400> SEQUENCE: 11
gacttcaggc tagcatcgat ccatgggtcg acttttttttt tttttttt                49

<210> SEQ ID NO 12
<211> LENGTH: 23
<212> TYPE: DNA
<213> ORGANISM: Artificial Sequence
<220> FEATURE:
<223> OTHER INFORMATION: Sense sequence "PA140_AUAP"

<400> SEQUENCE: 12
gacttcaggc tagcatcgat cca                                            23

<210> SEQ ID NO 13
<211> LENGTH: 19
<212> TYPE: DNA
<213> ORGANISM: Artificial Sequence
<220> FEATURE:
<223> OTHER INFORMATION: Sense sequence "PA141"

<400> SEQUENCE: 13
catcgatcca tgggtcgac                                                 19

<210> SEQ ID NO 14
<211> LENGTH: 20
<212> TYPE: DNA
<213> ORGANISM: Artificial Sequence
<220> FEATURE:
<223> OTHER INFORMATION: Sense sequence "AUAP (Gibco)"

<400> SEQUENCE: 14
ggccacgcgt cgactagtac                                                20

<210> SEQ ID NO 15
<211> LENGTH: 20
<212> TYPE: DNA
<213> ORGANISM: Artificial Sequence
<220> FEATURE:
<223> OTHER INFORMATION: Sense sequence "left1_Forward"

<400> SEQUENCE: 15
ggcacgaggt tacttgttgg                                                20
```

```
<210> SEQ ID NO 16
<211> LENGTH: 21
<212> TYPE: DNA
<213> ORGANISM: Artificial Sequence
<220> FEATURE:
<223> OTHER INFORMATION: Sense sequence "left2_Forward"

<400> SEQUENCE: 16
cgaggttact tgttggagga a                                          21

<210> SEQ ID NO 17
<211> LENGTH: 21
<212> TYPE: DNA
<213> ORGANISM: Artificial Sequence
<220> FEATURE:
<223> OTHER INFORMATION: Sense sequence "ATG1_Forward"

<400> SEQUENCE: 17
ttgtggacaa aatgaatgac g                                          21

<210> SEQ ID NO 18
<211> LENGTH: 20
<212> TYPE: DNA
<213> ORGANISM: Artificial Sequence
<220> FEATURE:
<223> OTHER INFORMATION: Sense sequence "ATG2_Forward"

<400> SEQUENCE: 18
aaaatgaatg acggccaagt                                            20

<210> SEQ ID NO 19
<211> LENGTH: 20
<212> TYPE: DNA
<213> ORGANISM: Artificial Sequence
<220> FEATURE:
<223> OTHER INFORMATION: Sense sequence "uniqueFOR"

<400> SEQUENCE: 19
tgctgcatca gtcaacaaca                                            20

<210> SEQ ID NO 20
<211> LENGTH: 18
<212> TYPE: DNA
<213> ORGANISM: Artificial Sequence
<220> FEATURE:
<223> OTHER INFORMATION: Sense sequence "TaqFOR"

<400> SEQUENCE: 20
tcatcctgcc cggtgcta                                              18

<210> SEQ ID NO 21
<211> LENGTH: 24
<212> TYPE: DNA
<213> ORGANISM: Artificial Sequence
<220> FEATURE:
<223> OTHER INFORMATION: Sense sequence "1445_FOR"

<400> SEQUENCE: 21
acaccgggtg gacaatatat tctt                                       24

<210> SEQ ID NO 22
<211> LENGTH: 27
<212> TYPE: DNA
<213> ORGANISM: Artificial Sequence
<220> FEATURE:
<223> OTHER INFORMATION: Sense sequence "StopORF_FOR"
```

-continued

```
<400> SEQUENCE: 22
ggtgcttaca ggcgtaatat taattag                                              27

<210> SEQ ID NO 23
<211> LENGTH: 26
<212> TYPE: DNA
<213> ORGANISM: Artificial Sequence
<220> FEATURE:
<223> OTHER INFORMATION: Sense sequence "3'UTR_FOR"

<400> SEQUENCE: 23
cggtgtcgat attatacatg ttacga                                               26

<210> SEQ ID NO 24
<211> LENGTH: 19
<212> TYPE: DNA
<213> ORGANISM: Artificial Sequence
<220> FEATURE:
<223> OTHER INFORMATION: Antisense sequence "CAATCH1_unique_REVERSE"

<400> SEQUENCE: 24
aggagtttcg cccattgag                                                       19

<210> SEQ ID NO 25
<211> LENGTH: 20
<212> TYPE: DNA
<213> ORGANISM: Artificial Sequence
<220> FEATURE:
<223> OTHER INFORMATION: Antisense sequence "Taq_CAATCH1_REVERSE"

<400> SEQUENCE: 25
caaggagttt cgcccattga                                                      20

<210> SEQ ID NO 26
<211> LENGTH: 24
<212> TYPE: DNA
<213> ORGANISM: Artificial Sequence
<220> FEATURE:
<223> OTHER INFORMATION: Antisense sequence "CAATCH1_2642_REV"

<400> SEQUENCE: 26
ctataaaatc aaacgcaaga ccat                                                 24

<210> SEQ ID NO 27
<211> LENGTH: 25
<212> TYPE: DNA
<213> ORGANISM: Artificial Sequence
<220> FEATURE:
<223> OTHER INFORMATION: Antisense sequence "CAATCH1_2727_REV"

<400> SEQUENCE: 27
tgttgcacag agttcttgaa gattt                                                25
```